(12) United States Patent
Mograbi et al.

(10) Patent No.: US 9,617,301 B2
(45) Date of Patent: *Apr. 11, 2017

(54) ANTIOXIDANT, ANTI-INFLAMMATORY, ANTI-RADIATION, METAL CHELATING COMPOUNDS AND USES THEREOF

(71) Applicants: Oneday-Biotech and Pharma Ltd., Tel Aviv (IL); Yissum Research Development Company of the Hebrew University of Jerusalem, Ltd., Jerusalem (IL)

(72) Inventors: Josef Mograbi, Tel Aviv (IL); Daphne Atlas, Jerusalem (IL); Shoshana Keynan, Modiine (IL)

(73) Assignees: ONEDAY-BIOTECH AND PHARMA LTD., Tel Aviv (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,476

(22) Filed: Apr. 21, 2015

(65) Prior Publication Data

US 2015/0218211 A1    Aug. 6, 2015

Related U.S. Application Data

(63) Continuation of application No. 14/323,576, filed on Jul. 3, 2014, now Pat. No. 9,034,824, which is a continuation of application No. 13/963,537, filed on Aug. 9, 2013, now Pat. No. 8,802,635, which is a continuation of application No. 13/947,744, filed on Jul. 22, 2013, now abandoned, which is a continuation of application No. PCT/IL2012/000032, filed on Jan. 19, 2012.

(60) Provisional application No. 61/469,138, filed on Mar. 30, 2011, provisional application No. 61/434,454, filed on Jan. 20, 2011.

(51) Int. Cl.
| | |
|---|---|
| *A61K 38/00* | (2006.01) |
| *A61K 38/03* | (2006.01) |
| *A61K 38/04* | (2006.01) |
| *A61K 38/07* | (2006.01) |
| *A61K 38/10* | (2006.01) |
| *A61K 8/64* | (2006.01) |
| *A61Q 90/00* | (2009.01) |
| *C07K 5/10* | (2006.01) |
| *C07K 7/00* | (2006.01) |
| *C07K 7/06* | (2006.01) |
| *C07K 7/08* | (2006.01) |
| *C07K 9/00* | (2006.01) |
| *C07K 5/103* | (2006.01) |
| *C07K 5/02* | (2006.01) |
| *A61K 38/16* | (2006.01) |
| *C07K 14/00* | (2006.01) |
| *A61Q 19/08* | (2006.01) |
| *A61K 47/48* | (2006.01) |

(52) U.S. Cl.
CPC .............. *C07K 5/1013* (2013.01); *A61K 8/64* (2013.01); *A61K 38/00* (2013.01); *A61K 38/03* (2013.01); *A61K 38/04* (2013.01); *A61K 38/07* (2013.01); *A61K 38/10* (2013.01); *A61K 38/16* (2013.01); *A61Q 19/08* (2013.01); *A61Q 90/00* (2013.01); *C07K 5/0202* (2013.01); *C07K 5/10* (2013.01); *C07K 7/00* (2013.01); *C07K 7/06* (2013.01); *C07K 7/08* (2013.01); *C07K 9/00* (2013.01); *C07K 14/00* (2013.01); *A61K 47/48038* (2013.01)

(58) Field of Classification Search
CPC ........ A61K 38/00; A61K 38/03; A61K 38/04; A61K 38/07; A61K 38/10; A61K 47/48038; A61K 8/64; A61Q 90/00; C07K 5/10; C07K 7/00; C07K 7/06; C07K 7/08; C07K 9/00
USPC .. 514/15.1, 15.7, 16.6, 17.7, 17.8, 18.6, 1.9, 514/20.8, 21.9, 6.9; 530/330
See application file for complete search history.

(56) References Cited

U.S. PATENT DOCUMENTS

| | | | |
|---|---|---|---|
| 4,966,848 A | 10/1990 | Smith et al. | |
| 5,223,421 A | 6/1993 | Smith et al. | |
| 5,837,218 A | 11/1998 | Peers et al. | |
| 5,874,468 A | 2/1999 | Atlas et al. | |
| 5,889,055 A | 3/1999 | Howard | |
| 5,928,926 A * | 7/1999 | Kurdi-Haidar | C12N 9/14 435/195 |
| 5,985,261 A | 11/1999 | White et al. | |
| 6,369,106 B1 | 4/2002 | Atlas et al. | |

(Continued)

FOREIGN PATENT DOCUMENTS

| | | |
|---|---|---|
| WO | 9533765 A1 | 12/1995 |
| WO | 99/62927 A1 | 12/1999 |

(Continued)

OTHER PUBLICATIONS

A0A078CKJ2 from UnitProt, pp. 1-3. Sequence updated on Oct. 29, 2014. Accessed Mar. 26, 2016.*

(Continued)

*Primary Examiner* — Julie Ha
(74) *Attorney, Agent, or Firm* — Vorys, Sater, Seymour and Pease LLP

(57) ABSTRACT

Potent compounds having combined antioxidant, anti-inflammatory, anti-radiation and metal chelating properties are described. Short peptides having these properties, and methods and uses of such short peptides in clinical and cosmetic applications are described.

14 Claims, 16 Drawing Sheets

(56) References Cited

U.S. PATENT DOCUMENTS

| | | | |
|---|---|---|---|
| 6,627,746 | B1 | 9/2003 | Doberstein et al. |
| 6,903,136 | B2 | 6/2005 | Miller et al. |
| 7,195,766 | B2 | 3/2007 | White |
| 7,307,063 | B2 | 12/2007 | Sharma et al. |
| 7,534,438 | B2 | 5/2009 | White |
| 8,735,343 | B2 | 5/2014 | White |
| 2006/0057188 | A1 | 3/2006 | Gaetani |
| 2007/0033666 | A1 | 2/2007 | Harris et al. |
| 2008/0009448 | A1 | 1/2008 | Sakurada |
| 2008/0069839 | A1 | 3/2008 | Guan et al. |
| 2009/0156508 | A1 | 6/2009 | Schteingart et al. |
| 2009/0285912 | A1 | 11/2009 | Rodriquez |
| 2011/0318380 | A1 | 12/2011 | Brix et al. |

FOREIGN PATENT DOCUMENTS

| | | |
|---|---|---|
| WO | 0234202 A2 | 5/2002 |
| WO | 02099084 A2 | 12/2002 |
| WO | 2004024868 A2 | 3/2004 |
| WO | 2004111636 A2 | 12/2004 |
| WO | 2005075679 A2 | 8/2005 |
| WO | 2005123108 A2 | 12/2005 |
| WO | 2010037395 A2 | 4/2010 |
| WO | 2014016831 A1 | 1/2014 |
| WO | 2014016837 A1 | 1/2014 |

OTHER PUBLICATIONS

Q85485 from UnitProt, pp. 1-3. Sequence updated on Nov. 1, 1996. Accessed Mar. 26, 2016.*

Water from www.biology-online.org/diectionary/Water, pp. 1-3. Accessed Apr. 24, 2014.*

N-acetylcysteine from http://www.naturalremedies.org/n-acetylcysteine/, pp. 1-6, accessed Feb. 1, 2016.

Vitamin C from http://www.globalhealingcenter.com/natural-health/foods-high-in-vitamin-c/, pp. 1-3. Accessed Feb. 1, 2016.

Amer et al., (2005) Red blood cells, platelets and polymorphonuclear neutrophils of patients with sickle cell disease exhibit oxidative stress that can be ameliorated by antioxidants. British Journal of Haematology 132(1): 108-113.

Amer et al., (2008) N-acetylcysteine amide (AD4) attenuates oxidative stress in beta-thalassemia blood cells. Biochim Biophys Acta 1780(2): 249-55.

Bachnoff et al., (2011) Alleviation of oxidative stress by potent and selective thioredoxin-mimetic peptides. Free Radic Biol Med 50(10): 1355-1367.

Ballatori et al., (2009) Glutathione dysregulation and the etiology and progression of human diseases. Biol Chem 390(3): 191-214.

Banerjee (2009) Hemolytic uremic syndrome. Indian Pediatr 46(12): 1075-84.

Bartov et al., (2006) Low molecular weight thiol amides attenuate MAPK activity and protect primary neurons from Aβ (1-42) toxicity. Brain Res 1069(1): 198-206.

Batt and Reske (2010) the Hospital Physician® Board Review Manuals, Hematology, vol. 5, Part 3 pp. 1-12, Hemoglobinopathies, published by Turner White Communications, Inc.

Behrends HW et al., (1996) Evaluation of the secondary structure of vaccinia-virus thymidine kinase by circular-dichroism spectroscopy of overlapping synthetic peptides. Eur J Biochem 241(1): 126-132.

Bolton-Maggs et al., (2004) Guidelines for the diagnosis and management of hereditary spherocytosis. Br J Haematol 126(4): 455-74.

Breuer et al., (2012) Non-transferrin bound iron in Thalassemia: differential detection of redox active forms in children and older patients. Am J Hematol 87(1): 55-61.

Cacciatore et al., (2010) Prodrug approach for increasing cellular glutathione levels. Molecules 15(3): 1242-64.

Calvani et al., (2003) The role of carnitine system in maintaining muscle homeostasis. Basic Appl Myol 13(3): 105-120.

Chassaing et al., (1999) Determination of reduced and oxidized homocysteine and related thiols in plasma by thiol-specific pre-column derivatization and capillary electrophoresis with laser-induced fluorescence detection. J Chromatogr B Biomed Sci Appl 735(2): 219-27.

Clay et al., (2001) Mitochondrial disease: a pulmonary and critical-care medicine perspective. Chest 120(2): 634-48.

Fibach (1998) Techniques for studying stimulation of fetal hemoglobin production in human erythroid cultures. Hemoglobin 22(5-6): 445-58.

Fibach and Rachmilewitz (2008) The role of oxidative stress in hemolytic anemia. Curr Mol Med 8(7): 609-19.

Fibach et al., (2010) Amelioration of oxidative stress in red blood cells from patients with beta-thalassemia major and intermedia and E-beta-thalassemia following administration of a fermented papaya preparation. Phytother Res 24(9): 1334-8.

Flanagan et al., (2010) Role of carnitine in disease. Nutr Metab (Lond) 7:30.

Fraternale et al., (2009) GSH and analogs in antiviral therapy. Mol Aspects Med 30(1-2): 99-110.

Gallagher (2004) Hereditary elliptocytosis: spectrin and protein 4.1R. Semin Hematol 41(2): 142-64.

Gehrs and Friedberg (2002) Autoimmune hemolytic anemia. Am J Hematol 69(4): 258-71.

Grinberg et al., (2005) N-acetylcysteine amide, a novel cell-permeating thiol, restores cellular glutathione and protects human red blood cells from oxidative stress. Free Radic Biol Med 38(1): 136-145.

Hess (2006) An update on solutions for red cell storage. Vox Sang 91(1): 13-9.

Hiatt et al., (1989) Carnitine and acylcarnitine metabolism during exercise in humans. Dependence on skeletal muscle metabolic state. J Clin Invest 84(4): 1167-1173.

Hudson (2001) Rethinking cystic fibrosis pathology: the critical role of abnormal reduced glutathione (GSH) transport caused by CFTR mutation. Free Radic Biol Med 30(12): 1440-61.

Kim et al., (2011) A novel dithiol amide CB3 attenuates allergic airway disease through negative regulation of p38 mitogen-activated protein kinase. Am J Respir Crit Care Med 183(8):1015-1024.

Kohne (2011) Hemoglobinopathies: clinical manifestations, diagnosis, and treatment. Dtsch Arztebl Int 108(31-32): 532-40.

Koren et al., (2008) Response to hydroxyurea therapy in beta-thalassemia. Am J Hematol 83(5): 366-70.

Krajcovicová-Kudláčková et al., (2000) Correlation of carnitine levels to methionine and lysine intake. Physiol Res 49(3): 399-402.

Liang and Nishino (2010) State of the art in muscle lipid diseases. Acta Myol 29(2): 351-6.

Liang and Nishino (2011) Lipid storage myopathy. Curr Neurol Neurosci Rep 11(1): 97-103.

Mingshan et al., (2008) Endoplasmic Reticulum Stress and Unfolded Protein Response in Atm-Deficient Thymocytes and Thymic Lymphoma Cells Are Attributable to Oxidative Stress1. Neoplasia 10(2): 160-167.

Muscular dystrophy association (MDA) Inc.,"Facts About Mitochondrial Myopathies", updated Dec. 2009.

Owen and Butterfield (2010) Measurement of oxidized/reduced glutathione ratio. Methods Mol Biol 648: 269-77.

Terrill et al., (2011) N-Acetylcysteine treatment of dystrophic mdx mice results in protein thiol modifications and inhibition of exercise induced myofibre necrosis. Neuromuscul Disord 22(5): 427-34.

Tiwari et al., (2009) Radiation-induced micronucleus formation and DNA damage in human lymphocytes and their prevention by antioxidant thiols. Mutat Res 31;676(1-2): 62-68.

Townsend et al., (2003) The importance of glutathione in human disease. Biomed Pharmacother 57(3-4): 145-55.

Vaz and Wanders (2002) Carnitine biosynthesis in mammals. Biochem J 361(Pt 3): 417-29.

Withers and King (1979) Proline: A Novel Cryoprotectant for the Freeze Preservation of Cultured Cells of *Zea mays* L. Plant Physiol 64(5): 675-8.

Wu et al., (2004) Glutathione metabolism and its implications for health. J Nutr 134(3): 489-92.

(56) References Cited

OTHER PUBLICATIONS

Acetate is naturally occurring salt, from www.britannica.com/EBchecked/topic/3235/acetic-acid-CH3COOH, pp. 1-6. Accessed Sep. 25, 2014.
Definition of Moiety From http://dictionary.reference.com/browse/moiety, pp. 1-3, accessed Aug. 26, 2010.
Water is natural product, from www.biology-online.org/dictionary/Water, pp. 1-3. Accessed Apr. 24, 2014.
LUu et al., (2009), Regulation of glutathione synthesis. Mol Aspects Med, 30(1-2): 42-59.

* cited by examiner

ANTIOXIDANT, ANTI-INFLAMMATORY, ANTI-RADIATION, METAL CHELATING COMPOUNDS AND USES THEREOF

FIELD OF THE INVENTION

The present invention relates to potent compounds having combined antioxidant, anti-inflammatory, anti-radiation and metal chelating properties. More specifically, the present invention relates to short peptides having said properties, and to methods and uses of such short peptides in clinical and cosmetic applications.

BACKGROUND OF THE INVENTION

The normal functioning of biological systems requires, inter alia, proper balance between formation and elimination of damaging substances. Oxidative stress, for example, represents an imbalance between the levels of damaging oxidizing species, such as reactive oxygen species (ROS) and reactive nitrogen species (RNS), in a biological system and the insufficient ability of that biological system to readily neutralize or eliminate the oxidizing species. Consequences of this stress include but are not limited to deleterious modification to cellular proteins, lipids and DNA.

Oxidative stress is associated with a wide range of diseases and other medical conditions, including for example Alzheimer's disease, Parkinson's disease, diabetes and pathologies secondary to diabetes, rheumatoid arthritis, neurodegeneration (particularly in motor neuron diseases), airway inflammation and hyper-responsiveness (for example, asthma), and some skin disorders, such as vitiligo.

In some of these cases, it is unclear whether the oxidative stress is the cause or the consequence of the medical condition. However, in many cases, lowering the oxidative stress leads to improvement in the disease manifestation. In many other cases, lowering the oxidative stress may prevent the disease outbreak. In addition to pathological conditions, oxidative stress is also known to be involved in some undesired components of aging.

Thiol (—SH) containing compounds are a type of molecules capable of neutralizing several types of damaging oxidative species, thus acting as reducing reagents. The activity of this group of compounds is mainly due to the sulfur atom they comprise which participates in nucleophilic attack on toxic electrophiles, scavenging free radicals, effecting repair of damaged targets through hydrogen atom donation, altering the redox status of the cell, or affecting gene transcription or protein function.

Thiol containing compounds include natural molecules, produced by all living organisms including animals and plants, as well as synthetic molecules. Examples of natural thiol containing antioxidants include glutathione, which is one of the most potent and important antioxidants in mammals, thioredoxins and cysteine.

Examples of synthetic thiol containing redox molecules include N-acetylcysteine amide, as described, for example, in Atlas et al., (2005) Free Radic Biol Med, Vol. 38(1), pp. 136-45. Another example is N-acetyl-cysteine-proline-cysteine-amide (CB3), described, for example, in Kim et al. (2011) 183(8):1015, which evaluated its protective properties in allergic airway diseases using an ovalbumin (OVA)-inhalation model in mice.

U.S. Pat. No. 5,874,468 discloses brain targeted low molecular weight, hydrophobic antioxidants and use of antioxidants in treatment of central nervous system neurodegenerative disorders such as Parkinson's, Alzheimer's and Creutzfeldt-Jakob's diseases and in treatment of conditions of peripheral tissues, such as acute respiratory distress syndrome, amyotrophic lateral sclerosis, atherosclerotic cardiovascular disease and multiple organ dysfunction, in which oxidants are overproduced.

U.S. Pat. No. 6,369,106 discloses a method of reducing oxidative stress in the brain of an organism having a blood brain barrier and suffering an ischemic brain injury, the method comprising the step of administering a compound to the organism, the compound having (a) a combination of molecular weight and membrane miscibility properties for permitting the compound to cross the blood brain barrier of the organism; (b) a readily oxidizable chemical group for exerting antioxidation properties; and (c) a chemical make-up for permitting the compound or its intracellular derivative to accumulate within the cytoplasm of cells.

International Patent Application Publication No. WO 2002/034202 discloses an antioxidant compound characterized by (a) a peptide including at least three amino acid residues of which at least two are cysteine residues, each having a readily oxidizable sulfhydryl group for effecting antioxidation; and at least two peptide bonds, each being cleavable by at least one intracellular peptidase; and (b) a first hydrophobic or non-charged moiety being attached to an amino terminal of the peptide via a first bond and a second hydrophobic or non-charged moiety being attached to a carboxy terminal of the peptide via a second bond, the first hydrophobic or non-charged moiety and the second hydrophobic or non-charged moiety are selected so as to provide the antioxidant compound with membrane miscibility properties for permitting the antioxidant compound to cross cellular membranes; wherein cleavage of the at least two peptide bonds by the at least one intracellular peptidase results in generation of a plurality of antioxidant species, each including one of the cysteine residues having the readily oxidizable sulfhydryl group and which is also active in effecting antioxidation, thereby providing for a plurality of different antioxidant species acting in synergy in exerting antioxidation.

Metal chelation is another important aspect in protecting biological systems from harmful substances. Metals, particularly heavy metals, are known to exert toxic effects when present in inappropriate amounts. Metal ions may generate free radicals reactions, thereby contributing to oxidative stress.

Ionizing radiation such as ultraviolet (UV) light, X rays, gamma rays, neutron beam and proton beam among others, may induce oxidative stress, inflammation, bone marrow damage (resulting in leukopenia, thrombocytopenia and anemia), digestive system damage (including loss of microvilli in the intestine walls) and abundant mutagenic and cytotoxic DNA lesions, which are responsible for the development of benign tumors, cancer (including hematological malignancies) and many other harmful conditions and disorders. Ionizing radiation promotes the production of free radicals, therefore antioxidants may protect against ionizing radiation-induced damage. It has been shown that antioxidant thiols (N-acetylcysteine amide, glutathione and thioproline) are capable of protecting against radiation-induced damage to cellular DNA in human blood lymphocytes (Tiwari et al. Mutat Res. 2009, 31;676(1-2):62-8). The various sources of natural ionizing radiation include cosmic radiation, solar radiation (including UV and protons) and high radon gas environments. The various sources of artificial ionizing radiation include external and internal radiation during medical procedures such as diagnostic imaging and scanning, injected or swallowed radioactive isotopes, nuclear medicine and radiation therapy, among others. There is an unmet need for improved compositions directed to the prevention and treatment of damages caused by ionizing radiation, suitable for oral, topical and systemic administration.

Additionally, there still remains a need for more effective means to handle conditions associated with excess amounts or excessive concentrations of damaging substances in cells. For example, it would be highly beneficial to have antioxidant, anti-inflammatory, anti-allergy and metal chelating compounds, with a combination of high potency, good stability, bioavailability and sufficient half life to achieve the desired effects.

SUMMARY OF THE INVENTION

The present invention provides short peptides having antioxidant, anti-inflammatory, anti-allergy, anti-radiation and metal chelating properties. The present invention further provides compositions, methods and uses of such short peptides in clinical and cosmetic applications.

The present invention discloses highly potent peptide compounds comprising unique dipeptide sequences located between two cysteine amino acid residues, and further comprising N-and C-terminal modifications. Typically, the amino and carboxy termini are blocked by appropriate blocking groups. Suitable amino terminal blocking groups include, but are not limited to, alkyl and acyl. Suitable carboxy terminal blocking groups include, but are not limited to, amide, ester and alcohol. Blocking groups exemplified herein include N-acetyl and C-terminal amide groups.

The peptides of the present invention were found to be highly effective in reducing inflammatory, as well as allergic responses in vivo, as exemplified hereinbelow. Surprisingly, the peptides of the present invention were found to be superior to known thiol-containing molecules, such as N-acetyl-cysteine-proline-cysteine-amide (also known as CB3) and N-acetyl-cysteine-glycine-proline-cysteine-amide (also known as CB4). The peptides of the present invention were shown to affect inflammatory-associated responses in the cellular level, by dramatically decreasing nuclear translocation of the nuclear factor-κB (NF-κB), and increasing cytoplasmic IkappaBalpha concentration in lung cells upon systemic inflammatory stimulation.

In addition, the peptides of the present invention were found to be highly effective in protecting keratinocytes against hydrogen peroxide-induced cytotoxicity, reducing ROS formation upon LPS administration in vivo, reversing oxidative stress-induced phosphorylation of p38 and JNK in model cells, and protecting cells against UVB-induced irradiation, as further exemplified hereinbelow.

The peptides of the present invention are able to cross membranes and enter cells very efficiently. Without wishing to be bound by any particular theory or mechanism of action, it is contemplated that the N-and C-termini modifications of the peptides of the present invention reduce their polarity, thus facilitating the ability of these peptides to cross cell membranes, enter easily into cells and to accumulate within the cells. In addition, the modifications may stabilize and protect the peptides from degradation, including for example enzymatic, chemical or biochemical breakdown of the molecules.

The properties of the short peptides of the present invention may be utilized in various applications. For example, such peptides may have therapeutic applications in the treatment and/or prevention of diseases and disorders associated with oxidative stress, and/or in the treatment and/or prevention of diseases and disorders associated with inflammation, and/or accumulation of metal ions. In addition, peptides of the present invention may be used not only as anti-inflammatory but also as anti-allergic agents. The properties of the peptides of the present invention may also be utilized in anti-aging treatments and cosmetic applications, such as cosmetic compositions.

According to one aspect, the present invention provides a peptide having an amino acid sequence selected from the group consisting of:

Cys-Lys-Met-Cys, (SEQ ID NO: 1)

Cys-Met-Lys-Cys; (SEQ ID NO: 2)
and

Cys-β-Ala-His-Cys. (SEQ ID NO: 3)

In some embodiments, a tetra-peptide is provided, selected from the group consisting of:

Cys-Lys-Met-Cys, (SEQ ID NO: 1)

Cys-Met-Lys-Cys; (SEQ ID NO: 2)
and

Cys-β-Ala-His-Cys. (SEQ ID NO: 3)

In some embodiments, the peptide further comprises at least one modification of the peptide's terminus According to some embodiments, the peptide comprises an amino-terminal modification. According to other embodiments, the peptide comprises a carboxy-terminal modification. According to yet other embodiments, the peptide comprises both amino-terminal and carboxy-terminal modifications. Each possibility represents a separate embodiment of the invention.

In principle, any group suitable for amino terminus modification, and any group suitable for carboxy terminus modification may be used for the peptide of the present invention.

In some embodiments, the amino terminal modification is an amino terminal blocking group.

In some typical embodiments, the amino-terminal blocking group is selected from the group consisting of alkyl and acyl. Each possibility represents a separate embodiment of the invention.

In some exemplary embodiments, the amino-terminal blocking group is an acetyl group.

In some embodiments of the present invention, the amino terminal modification is a moiety that improves the ability of the peptide to penetrate lipid layers and/or improves the ability of the peptide to penetrate into the skin. Such moiety may provide high efficacy topical administration. In some exemplary embodiments, the moiety that improves that ability of the peptide to penetrate lipid layers and/or improves its ability to penetrate the skin is a fatty acid. In some embodiments, the fatty acid is selected from the group consisting of palmitic acid, phosphatidic acid, stearic acid, arachidonic acid, docosahexaenoic acid, eicosapentaenoic acid, and oleic acid. Each possibility represents a separate embodiment of the invention.

In some embodiments, the amino terminal modification is selected from the group consisting of an amino terminal blocking group and a fatty acid. Each possibility represents a separate embodiment of the invention.

In some embodiments, the amino terminal modification is selected from the group consisting of alkyl, acyl and a fatty acid.

In some embodiments, the carboxy terminal modification is a carboxy terminal blocking group. In some typical embodiments, the carboxy terminal blocking group is selected from the group consisting of amide, ester and alcohol group. Each possibility represents a separate embodiment of the invention. In some exemplary embodiments, the carboxy terminal blocking group is an amide group.

In some embodiments, the peptide is cleavable by intracellular peptidases. The cleavage of the peptide upon entry into cells may result in molecules that exhibit antioxidant, anti-inflammatory and metal chelation properties and activities.

In some additional or alternative embodiments, the N-and/or C-terminal modifications are hydrolysable by intracellular enzymes. Thus, these modifications may be hydrolyzed upon entry of the peptide into cells.

In some embodiments of the present invention, the middle dipeptide, located between the two Cys residues, is selected from the group consisting of Lys-Met and Met-Lys. Each possibility represents a separate embodiment of the invention. Lysine and methionine are precursors for the biosynthesis of carnitine molecules. In living cells, carnitine is required for the transport of fatty acids from the cytosol into the mitochondria where the breakdown of lipids takes place during the generation of metabolic energy. Carnitine is also known to have strong antioxidant activity. As noted above, the peptide may be cleaved by peptidases upon entry into cells. In some embodiments, the peptide undergoes cleavage that results in the release of lysine and methionine. In some embodiments, administration of the peptide may promote the formation of carnitine and may increase the amount and concentration of carnitine in cells. Such peptide may be used in a method for increasing the amount and concentration of carnitine in cells.

In some embodiments of the present invention, the dipeptide β-Ala-His is located between the two Cys residues. The dipeptide β-Ala-His (β-alanyl-L-histidine) is known as carnosine. Carnosine is capable of performing a variety of functions, including anti-oxidation, anti-glycation, pH buffering and chelation of divalent metal cations. In some embodiments, the peptide undergoes intracellular cleavage that results in the release of free carnosine. In some embodiments, administration of the peptide may increase the amount and concentration of carnosine in cells. Such peptide may be used in a method for increasing the amount and concentration of carnosine in cells.

In some exemplary embodiments, the peptide N-acetyl-Cys-Lys-Met-Cys-amide (SEQ ID NO: 4) is provided.

In additional exemplary embodiments, the peptide N-acetyl-Cys-Met-Lys-Cys-amide (SEQ ID NO: 5) is provided.

In yet additional exemplary embodiments, the peptide N-acetyl-Cys-β-Ala-His-Cys-amide (SEQ ID NO: 6) is provided.

In some embodiments of the present invention, the peptide has an activity selected from the group consisting of antioxidant, anti-inflammatory, anti-allergy, anti-radiation, metal chelation or combinations thereof. Each possibility represents a separate embodiment of the invention.

In some embodiments of the present invention, the peptide has an anti-inflammatory activity. In some embodiments of the present invention, the peptide has an anti-allergic activity. In some embodiments of the present invention, the peptide has an anti-oxidant activity.

In some embodiments of the present invention, the peptide is in the form of a salt. In some embodiments, the salt is selected from the group consisting of trifluoroacetic acid (TFA), acetate and citrate salts. Each possibility represents a separate embodiment of the invention.

According to another aspect, the present invention provides a composition comprising a peptide of the present invention or a salt thereof.

In some embodiments of the present invention, the peptide is formulated as a pharmaceutical composition. According to these embodiments, the composition further comprises a pharmaceutically acceptable diluent, solvent, excipient or carrier.

In some embodiments of the present invention, the peptide is formulated as a cosmetic composition. According to these embodiments, the composition further comprises a cosmetically acceptable diluent, solvent, excipient or carrier.

Any suitable route of administration may be used for the composition of the present invention, including but not limited to local and systemic routes. Systemic administration includes all enteral and all parenteral routes. Non-limiting examples of suitable administration routes include topical application, oral, rectal, transmucosal such as transnasal and buccal, intravenous, intramuscular, transdermal, subcutaneous, intradermal, intravitreal, intravesicular and inhalation routes.

Thus, in some embodiments, the composition of the present invention is formulated for topical administration. In other embodiments, the composition is formulated for systemic administration.

The compositions of the present invention are useful for the treatment or prevention of diseases and disorders associated with oxidative stress. The compositions of the present invention are also useful for the treatment or prevention of diseases and disorders associated with inflammation and/or allergy. In addition, the compositions of the present invention are useful for the treatment or prevention of diseases and disorders associated with the presence or accumulation of advanced glycation end products, also known as non-enzymatic glycosylation products. In addition, the compositions of the present invention are useful for the treatment or prevention of diseases and disorders associated with the presence or accumulation of metal ions. The compositions of the present invention are also useful for the treatment or prevention of damages caused by ionizing radiation.

Thus, according to another aspect, the present invention provides a method for treating a disease or disorder associated with at least one of oxidative stress, allergy or inflammation, the method comprising administering to a subject in need a composition comprising a peptide of the present invention or a salt thereof. According to certain embodiments, the method comprises administering mixtures of peptides of the invention.

In some embodiments of the present invention, a pharmaceutical composition is provided, comprising at least one peptide of the present invention or at least one salt thereof as an active ingredient, for use in the treatment of a disease or disorder associated with at least one of oxidative stress, allergy (chronic and/or acute flare) or inflammation (chronic and/or acute flare).

In some embodiments, the disease or disorder is associated with oxidative stress. In some embodiments, the disease or disorder associated with oxidative stress is selected from the group consisting of Alzheimer's disease, Parkinson's disease, diabetes, rheumatoid arthritis, ischemia-reperfusion injury and vitiligo. Each possibility represents a separate embodiment of the invention. The diabetes may include type I and type II diabetes. Each possibility represents a separate embodiment of the invention.

In some embodiments, the disease or disorder is associated with inflammation. In some embodiments, the disease or disorder associated with inflammation is an auto-immune disease. In some embodiments, the disease or disorder associated with inflammation is selected from the group consisting of acute inflammation, rheumatoid arthritis, an inflammatory bowel disease and atherosclerosis. Each possibility represents a separate embodiment of the invention.

In some embodiments, the disease or disorder is associated with allergy. In some embodiments, the disease or disorder associated with allergy is selected from the group consisting of an allergic airway disease, allergic rhinitis, eczema, dermatitis, a gastrointestinal food allergy and an ocular allergy. Each possibility represents a separate embodiment of the invention. In some embodiments, the allergic disease is asthma.

According to another aspect, the present invention provides a method for treating a disease or disorder associated with the presence or accumulation of advanced glycation end products, the method comprising administering to a subject in need thereof a composition comprising as active ingredient a peptide of the present invention or a salt thereof According to certain embodiments, the method comprises administering mixtures of peptides of the invention.

In some embodiments of the present invention, a pharmaceutical composition is provided, comprising at least one peptide of the present invention or at least one salt thereof as an active ingredient, for use in the treatment and/or prevention of diseases or disorders associated with the presence or accumulation of advanced glycation end products.

In some embodiments, the disease or disorder associated with the presence or accumulation of advanced glycation end products is selected from the group consisting of diabetes, cataract, heart failure, hypertension and callused skin. Each possibility represents a separate embodiment of the invention. The diabetes may include type I and type II diabetes. Each possibility represents a separate embodiment of the invention.

In some embodiments of the present invention, the disease or disorder is a skin condition and/or cosmetic issue. In some exemplary embodiments, the skin condition is vitiligo.

In some embodiments, the present invention provides the use of a peptide of the present invention or a salt thereof as an anti-inflammatory agent.

In additional embodiments, the present invention provides the use of a peptide of the present invention or a salt thereof as an anti-allergic agent.

In additional embodiments, the present invention provides the use of a peptide of the present invention or a salt thereof as an antioxidant.

According to another aspect, the present invention provides a method for treating a disease or disorder associated with the presence or accumulation of metal ions, the method comprising administering to a subject in need thereof a pharmaceutical composition comprising as an active ingredient a peptide of the present invention or a salt thereof.

In some embodiments of the present invention, a pharmaceutical composition is provided, comprising at least one peptide of the present invention or at least one salt thereof as an active ingredient, for use in the treatment of a disease or disorder associated with the presence or accumulation of metal ions.

In some embodiments, the disease or disorder associated with the presence or accumulation of metals ions is selected from the group consisting of a liver disorder, Alzheimer's disease, heart attack (myocardial infarction), stroke and a prion disease. Each possibility represents a separate embodiment of the invention.

The antioxidant properties of the peptides of the present invention may be utilized in cosmetic applications, for skin care and protection. For example, the peptides of the present invention may be utilized as anti-aging agents.

Thus, according to yet another aspect, the present invention provides a method for slowing the aging process of the human skin, reducing the signs of aging of the human skin or both, the method comprising applying to the skin a cosmetic composition comprising the peptide of the present invention or a salt thereof.

In some embodiments, slowing the aging process of the human skin and reducing the signs of aging of the human skin encompass improvement of the skin tone, reduction of wrinkles, removal of lines, promotion of skin firmness and/or reduction of skin sensitivity and irritability.

In some embodiments, a cosmetic composition is provided, comprising a peptide of the present invention or a salt thereof as active ingredient, for use in slowing the aging process of the human skin, reducing the signs of aging of the human skin or both.

According to yet another aspect, the present invention provides a method for the prevention or treatment of a disorder or harmful effects caused by ionizing radiation comprising administering to a subject in need thereof a composition comprising a peptide of the present invention or a salt thereof. According to some embodiments, the method comprises administering mixtures of peptides of the present invention. According to some embodiments the compositions are administered in order to prevent or reduce at-least some of the harmful effects of radiation. According to other embodiments the compositions are administered to ameliorate at-least some of the harmful effects of prior exposure to radiation.

According to yet another aspect the present invention provides a composition for the prevention or treatment of at-least some of the harmful effects caused by ionizing radiation comprising a peptide of the present invention or a salt thereof. According to some embodiments, the composition comprises a mixture of peptides of the present invention.

According to some embodiments, ionizing radiation is selected from the group consisting of x-rays radiation, gamma-radiation, ultraviolet radiation, thermal radiation, nuclear radiation, cosmic radiation, or a combination thereof. Each possibility represents a separate embodiment of the invention. In some embodiments, the ionizing radiation is ultraviolet radiation. In some exemplary embodiments, the ultraviolet radiation is UVB.

According to some embodiments, the composition is administered within 24 hours before the exposure to the ionizing radiation or at about the time of exposure to the ionizing radiation and/or within 24 hours after the exposure to the ionizing radiation. According to alternative embodiments, the composition is administered within 12 hours, within six hours or within three hours or less before and/or after the exposure to the ionizing radiation. Each possibility represents a separate embodiment of the present invention.

DETAILED DESCRIPTION OF THE INVENTION

Figure 1:
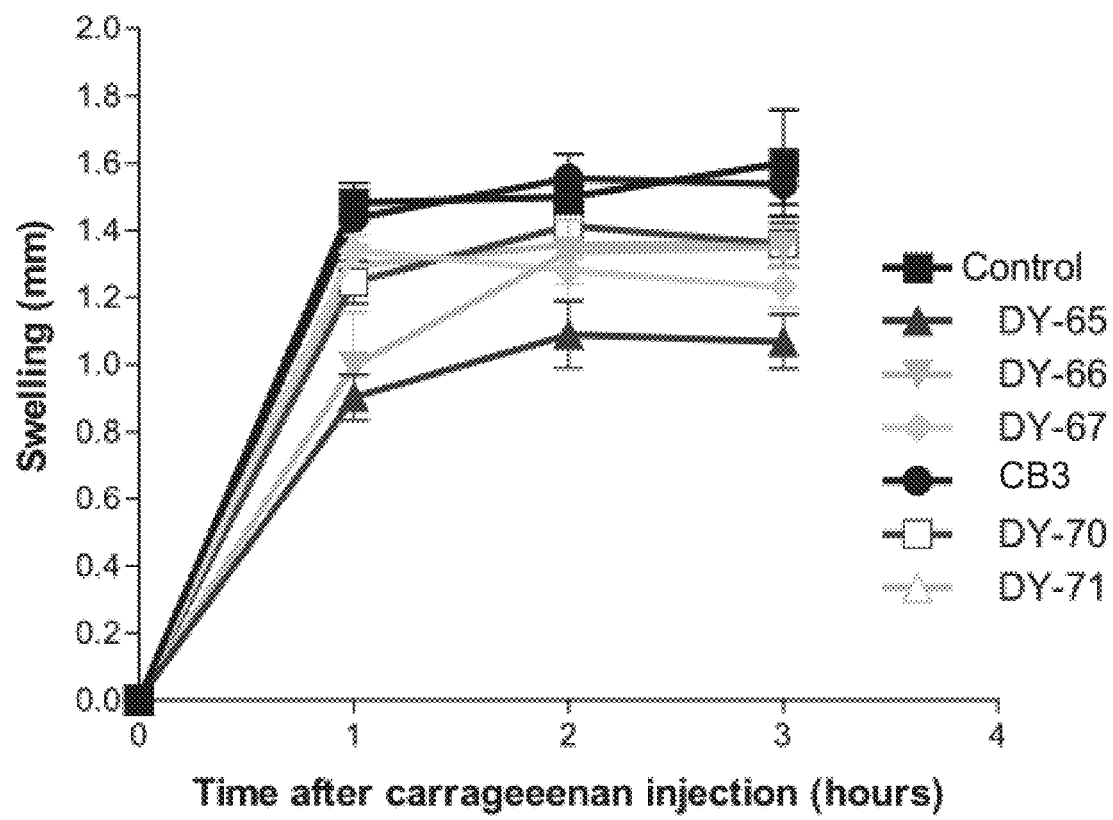
FIG. 1. Effect of peptides on carrageenan-induced hind paw swelling.

The present invention discloses short peptides having antioxidant, anti-inflammatory, anti-allergy, anti-radiation and metal chelating properties, and their use in therapeutic, preventive and cosmetic applications.

The peptides of the present invention show a desirable combination of properties such as ability to enter cells, stability inside the cells, high potency and low toxicity.

Definitions

As used herein "peptide" indicates a sequence of amino acids linked by peptide bonds. The term "tetra-peptide" indicates a peptide composed of four amino acids. The peptides of the present invention are typically utilized in a linear form, although it will be appreciated that in cases where cyclization does not severely interfere with peptide characteristics, cyclic forms of the peptide can also be utilized.

The term "amino acid" refers to compounds, which have an amino group and a carboxylic acid group, preferably in a 1,2-1,3-, or 1,4-substitution pattern on a carbon backbone. The term encompasses natural, non-natural and/or chemically modified amino acid residues. Natural amino acids include those found in proteins, which are L-amino acids. Non-natural and/or chemically modified amino acids include, for example, the corresponding N-methyl amino acids, side chain modified amino acids and the biosynthetically available amino acids which are not found in proteins (e.g., 5-hydroxy-lysine). The amino acid residues are represented throughout the specification and claims by either one or three-letter codes, as is commonly known in the art. The amino acids used in this invention are those which are available commercially or are available by routine synthetic methods. Certain residues may require special methods for incorporation into the peptide, and either sequential, divergent or convergent synthetic approaches to the peptide sequence are useful in this invention.

Also included within the scope of the invention are salts of the peptides, and derivatives of the peptides of the invention.

As used herein the term "salts" refers to salts of carboxyl groups and to acid addition salts of amino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, acetic acid or oxalic acid. Additional examples of suitable salts include trifluoroacetic acid (TFA), acetate and citrate salts.

Esters and amides of carboxy groups and acyl and alkyl derivatives of amino groups may be introduced into the molecule by reacting targeted amino acid residues of the peptide with an organic derivatizing agent that is capable of reacting with terminal residues. Preferred chemical derivatives include peptides that have been C-termini amidated or N-termini acetylated.

"Derivatives" of the peptides of the invention as used herein covers derivatives which may be prepared from the functional groups which occur as side chains on the residues or the N-or C-terminal groups, by means known in the art, and are included in the invention as long as they remain pharmaceutically/cosmetically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups).

"Permeability" refers to the ability of an agent or substance to penetrate, pervade, or diffuse through a barrier, membrane, or a skin layer. A "cell permeability", "cell-penetration" or "permeability-enhancing" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds. The permeability-enhancing moiety may be connected to any position in the peptide moiety, directly or through a spacer, preferably to the amino or carboxy terminus of the peptide moiety.

As used herein, the term "diseases and disorders associated with oxidative stress" refers to diseases and disorders caused and/or exacerbated by oxidative stress, or diseases and disorders characterized by abnormal increased oxidative stress.

As used herein, the terms "diseases and disorders associated with allergy", "allergic diseases" and "allergic disorders" are used interchangeably and refer to diseases and disorders characterized by hypersensitivity and hyper-responsiveness of the immune system to one or more foreign substances that are normally harmless (termed allergens). Allergic reactions are typically characterized by excessive activation of mast cells, basophils and eosinophils by Immunoglobulin E (IgE) antibodies.

As used herein, the terms "diseases and disorders associated with inflammation" and "inflammatory diseases/disorders" are used interchangeably and refer to diseases or disorder characterized by inflammation. The term encompasses both acute and chronic inflammation.

As used herein, the term diseases and disorders associated with the presence or accumulation of advanced glycation end-products (AGE) refers to diseases and disorders caused and/or exacerbated by AGE, or diseases and disorders characterized by accelerated formation of AGE and/or abnormal increased levels of AGE.

The term "advanced glycation end-products" (AGE) refers to a heterogeneous group of molecules formed from non-enzymatic reactions of reducing sugars (typically glucose or fructose) with free amino groups of proteins, lipids and nucleic acids. Certain reactive or precursor AGEs are able to form covalent crosslinks between proteins, which alters their structure and function, As used herein, the term "diseases and disorders associated with presence or accumulation of metal ions" refers to diseases and disorders caused and/or exacerbated by the presence or accumulation of metal ions, or diseases and disorders characterized by abnormal increased amounts or concentrations of metal ions.

As used herein, "treating" and "treatment", refers to reduction, amelioration or even elimination of at least some of the symptoms associated with the relevant disease. The term may include reduction of oxidative stress; inhibition or reduction of inflammation; inhibition or reduction of allergic reactions; reduction in the level or concentration of advanced glycation end products and/or neutralizing or lowering advanced glycation end products damage; and/or reduction in the level of damaging metals and/or neutralizing or lowering metal ion damage.

Peptides of the Present Invention

According to one aspect, the present invention provides a peptide having an amino acid sequence selected from the group consisting of:

```
                                              (SEQ ID NO: 1)
        Cys-Lys-Met-Cys, (SEQ ID NO: 2)
        Cys-Met-Lys-Cys, (SEQ ID NO: 3)
        Cys-β-Ala-His-Cys, ((SEQ ID NO: 7)
        Cys-γ-Glu-Cys-Cys (SEQ ID NO: 8)
        Cys-γ-Glu-Cys.
```

Each possibility represents a separate embodiment of the invention.

In some embodiments, the peptide is selected from the group consisting of:

```
                                              (SEQ ID NO: 1)
        Cys-Lys-Met-Cys, (SEQ ID NO: 2)
        Cys-Met-Lys-Cys;
        and (SEQ ID NO: 3)
        Cys-β-Ala-His-Cys.
```

It is understood that Cys represents the amino-acid cysteine; Lys represents the amino-acid lysine; Met represents the amino-acid methionine; β-Ala represents the amino-acid β-alanine; and γ-Glu represents the amino-acid γ-glutamic acid/γ-glutamate.

In some embodiments, the peptide further comprising at least one modification selected from the group consisting of an amino-terminal modification and a carboxy-terminal modification. According to these embodiments, the peptide is selected from the group consisting of:

```
                                              (SEQ ID NO: 9)
        Z-Cys-Lys-Met-Cys-Y, (SEQ ID NO: 10)
        Z-Cys-Met-Lys-Cys-Y;
        and (SEQ ID NO: 11)
        Z-Cys-β-Ala-His-Cys-Y,
``` wherein Z represents an amino terminal modification and Y represents a carboxy terminal modification.

In some embodiments, the N-and C-termini modifications reduce the polarity of the peptides of the present invention, thus facilitating the ability of these peptides to cross cell membranes, enter easily into cells and accumulate within the cells. In addition, modifications of the peptide termini may improve bio-stability, for example by blocking the action of peptidases.

The amino and carboxy termini modifications may be chosen from any amino and carboxy termini modifications conventionally used in the art of peptide chemistry, which will not adversely affect the activities of the peptide.

In some embodiments, the amino terminal modification comprises addition of an amino terminal blocking group.

Blocking of the N terminus may be performed, for example, by alkylation or acylation, using methods well known in the art. Non-limiting examples of suitable N-terminal blocking groups include $C_1$-$C_5$ branched or unbranched alkyl groups, acyl groups such as formyl and acetyl groups, and substituted forms thereof, such as the acetamidomethyl (Acm) group. Each possibility represents a separate embodiment of the invention.

In some embodiments of the present invention, the amino terminal modification comprises covalently linking to the N-terminus of the peptide a moiety that improves the ability of the peptide to penetrate lipid layers and/or improves the ability of the peptide to penetrate into the skin. Such moiety may provide high efficacy topical administration. In some exemplary embodiments, the moiety is a fatty acid. The fatty acid may be selected from the group consisting of palmitic acid, phosphatidic acid, stearic acid, arachidonic acid, docosahexaenoic acid, eicosapentaenoic acid and oleic acid. Each possibility represents a separate embodiment of the invention.

In some typical embodiments, the amino terminal modification is selected from the group consisting of acetyl, alkyl, acyl and a fatty acid. Each possibility represents a separate embodiment of the invention.

In some embodiments, the carboxy terminal modification is a carboxy terminal blocking group.

Blocking of the C terminus may be performed, for example, by amidation, reduction or esterification, using methods well known in the art. Non-limiting examples of suitable C-terminal blocking groups include amide, ester, and alcohol groups. Each possibility represents a separate embodiment of the invention.

Upon entry of the peptides into cells they may undergo cleavage by intracellular peptidases. The cleavage may result in molecules that still exert antioxidant, anti-inflammatory, anti-glycation and metal chelation properties and activities.

In addition, the N-and/or C-termini modifications of the peptides may be hydrolyzed, which may result in their accumulation in the cytosol.

In some embodiments the middle dipeptide, located between the two Cys residues, is selected from the group consisting of Lys-Met and Met-Lys. In some embodiments, a peptide is provided, selected from the group consisting of Cys-Lys-Met-Cys (SEQ ID NO: 1) and Cys-Met-Lys-Cys (SEQ ID NO: 2).

In some exemplary embodiments, the peptide N-acetyl-Cys-Lys-Met-Cys-amide (SEQ ID NO: 6) is provided.

In additional exemplary embodiments, the peptide N-acetyl-Cys-Met-Lys-Cys-amide (SEQ ID NO: 7) is provided.

In some embodiments the dipeptide β-Ala-His, is located between the two Cys residues. In some embodiments, a peptide Cys-β-Ala-His-Cys (SEQ ID NO: 3) is provided. In some exemplary embodiments, the peptide N-acetyl-Cys-β-Ala-His-Cys-amide (SEQ ID NO: 8) is provided.

In some embodiments, the dipeptide γ-Glu-Cys is located between the two Cys residues. In some embodiments, γ-Glu is located between the two Cys residues.

In some exemplary embodiments, a peptide is provided, selected from the group consisting of N-acetyl-Cys-γ-Glu-Cys-Cys-amide (SEQ ID NO: 12) and N-acetyl-Cys-γ-Glu-Cys-amide (SEQ ID NO: 13).

In some embodiments, the peptide itself and/or its metabolites have an activity selected from the group consisting of antioxidant, anti-inflammatory, anti-allergy and metal chelating or a combination thereof. Each possibility represents a separate embodiment of the invention.

The peptides of the present invention may be capable of chelating a wide variety of metal ions. Non-limiting examples of metal ions include Cu, Fe, Cd, Zn, Mg, Hg, Pb, As, Tl, Au. In some embodiments, the peptide is capable of chelating at least one metal ion selected from the group consisting of Cu and Fe. Each possibility represents a separate embodiment of the invention.

In some embodiments, the peptide has an anti-inflammatory activity. In additional embodiments, the peptide has an anti-allergic activity.

The peptides of the present invention may be synthesized by any technique known to those skilled in the art of peptide synthesis. These methods include solid phase as well as solution phase synthesis methods.

Solid phase peptide synthesis procedures are well known in the art and further described by John Morrow Stewart and Janis Dillaha Young, Solid Phase Peptide Syntheses (2nd Ed., Pierce Chemical Company, 1984).

A skilled artesian may synthesize any of the peptides of the present invention by using an automated peptide synthesizer using standard chemistry such as, for example, t-Boc or Fmoc chemistry.

The methods include exclusive solid phase synthesis, partial solid phase synthesis methods, fragment condensation, classical solution synthesis.

Synthetic peptides can be purified by preparative high performance liquid chromatography (Creighton T. (1983) Proteins, structures and molecular principles. W H Freeman and Co. N.Y.) and the composition of which can be confirmed via amino acid sequencing. Some of the peptides of the invention, which include only natural amino acids, may further be prepared using recombinant DNA techniques known in the art. The conjugation of the peptidic and permeability moieties may be performed using any methods known in the art, either by solid phase or solution phase chemistry. Some of the compounds of the present invention may conveniently be prepared using solution phase synthesis methods. Other methods known in the art to prepare compounds like those of the present invention can be used and are comprised in the scope of the present invention.

The permeability-enhancing moiety of the present invention may be connected to any position in the peptide moiety, directly or through a spacer. According to a specific embodiment, the cell-permeability moiety is connected to the amino terminus of the peptide moiety. The optional connective spacer may be of varied lengths and conformations comprising any suitable chemistry including but not limited to amine, amide, carbamate, thioether, oxyether, sulfonamide bond and the like. Non-limiting examples for such spacers include amino acids, sulfone amide derivatives, amino thiol derivatives and amino alcohol derivatives.

Cyclic versions of the peptides disclosed herein are also within the scope of the present invention. Cyclization of peptides may take place by any means known in the art, for example through free amino and carboxylic groups present in the peptide sequence, or through amino acids or moieties added for cyclization. Non limiting examples of cyclization types are: side chain to side chain cyclization, C-to-N terminal cyclization, side chain to terminal cyclization, and any type of backbone cyclization incorporating at least one N -ω-substituted amino acid residue/s as described for example in WO 95/33765.

Other methods known in the art to prepare peptides like those of the present invention can be used and are within the scope of the present invention.

In some embodiments, the peptide is in the form of a salt. Non-limiting examples of suitable salts include trifluoroacetic acid (TFA), acetate and citrate salts.

Compositions of the Present Invention

According to another aspect, the present invention provides a composition comprising the peptide of the present invention or a salt thereof.

In some embodiments, the composition is formulated as a pharmaceutical composition. According to these embodiments, the composition further comprises a pharmaceutically acceptable diluent, excipient or carrier.

In other embodiments, the composition is formulated as a cosmetic composition. According to these embodiments, the composition further comprises a cosmetically acceptable diluent, excipient or carrier.

In some embodiments, the composition further comprises at least one more active ingredient.

In some embodiments, a pharmaceutical composition is provided, consisting of the peptide of the present invention as an active ingredient. In additional embodiments, a cosmetic composition is provided, consisting of the peptide of the present invention as an active ingredient.

The peptide of the present invention or a salt thereof, and optionally additional one or more active ingredients, are present in the compositions of the present invention in an amount effective to achieve the intended purpose, for example, in an amount effective to treat a certain disease.

Any suitable route of administration may be used for the composition of the present invention, including but not limited to local and systemic routes. Systemic administration includes all enteral and all parenteral routes. Non-limiting examples of suitable administration routes include topical application, oral, rectal, transmucosal such as transnasal and buccal, intravenous, intramuscular, transdermal, subcutaneous, intradermal, intravitreal, intravesicular and inhalation routes.

Thus, in some embodiments, the composition of the present invention is formulated for topical administration. In other embodiments, the composition is formulated for systemic administration.

Cosmetic and pharmaceutical compositions of the present invention may be formulated in conventional manners. The proper formulation is dependent upon the route of administration chosen.

In some embodiments, the compositions of the present invention are formulated for topical use. Non-limiting examples of formulations for topical use include cream, ointment, lotion, gel, foam, suspension, aqueous or cosolvent solutions, salve, liposome and sprayable liquid form. The composition may also form part of a patch for transdermal application. Other suitable topical product forms for the compositions of the present invention include, for example, emulsion, mousse, lip balm, lip gloss, lotion, mask, pomade, solution and serum.

In some embodiments, the cosmetic or pharmaceutical compositions are formulated in the form of a solid or soft gel, for example, an aqueous-alcoholic gel and a clear gel. Typically, the aqueous phase comprises one or more gelling agents, for example cellulose gelling agents, or synthetic gelling agents.

In some embodiments, the compositions of the present invention are formulated for oral administration. Non-limiting examples of formulations for oral administration include tablets, pills, dragees, capsules, liquids, gels, syrups, slurries, suspensions, and the like, for oral ingestion by a patient. Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carboxymethylcellulose, and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

For administration by injection, the active ingredients of the composition may be formulated in aqueous solutions, for example in physiologically compatible buffers including but not limited to Hank's solution, Ringer's solution, or physiological salt buffer. Formulations for injection may be presented in unit dosage forms, for example, in ampoules, or in multi-dose containers with, optionally, an added preservative. The compositions may be in the form of suspensions, solutions, or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, for example, a sterile, pyrogen-free, water-based solution, before use.

For transmucosal administration, penetrants appropriate to the barrier to be permeated are used in the formulation. Such penetrants are generally known in the art.

For buccal administration, the compositions may take the form of tablets or lozenges formulated in conventional manner.

For administration by inhalation route, the active ingredients are conveniently delivered in the form of an aerosol spray presentation from a pressurized pack or a nebulizer with the use of a suitable propellant, for example, dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

In some embodiments, the compositions of the present invention are formulated for rectal administration, for example, as suppositories or retention enemas, using, for example, conventional suppository bases such as cocoa butter or other glycerides.

The exact formulation, route of administration, and dosage can be chosen by the individual physician in view of the patient's condition.

In some embodiments, the composition further comprises at least one additive useful in the cosmetic and pharmaceutical fields, including, but not limited to fats, emulsifiers and co-emulsifiers, hydrophilic or lipophilic gelling agents, colorants, fragrances, emollients, humectants, preservatives, vitamins, chelators, solvents, fillers, thickeners, hydrophilic and lipophilic filters, dyestuffs, neutralizers, penetration-enhancing agents and polymers.

Non-limiting examples of suitable fats include mineral oils, oils of animal origin (lanolin), synthetic oils (isopropyl myristate, octyldodecyl, isostearyl isostearate, decyl oleate or isopropyl palmitate), silicone oils (cyclomethicone or dimethicone) and fluorinated oils. Fatty alcohol, fatty acids, waxes and gums, notably silicone gums and elastomers can also be used as fats.

Non-limiting examples of suitable emulsifiers and co-emulsifiers include polyglycerol fatty acid esters, sucrose fatty acid esters, sorbitan fatty acid esters, oxyethylene sorbitan fatty acid esters, PEG fatty alcohol ethers, glycerol fatty acid esters, alkyl sulphates, alkyl ether sulphates, alkyl phosphates, alkyl polyglucosides and dimethicone copolyols.

Non-limiting examples of suitable hydrophilic gelling agents include carboxyvinyl polymers (carbomer), acrylic copolymers such as acrylate/alkylacrylate copolymers, polyacrylamids, polysaccharides such as xanthan gum, guar gum, natural gums such as cellulose gum and derivatives, clays and 2-acrylamido-2-methylpropane acid copolymers.

Non-limiting examples of suitable lipophilic gelling agents include modified clays such as bentones, fatty acid metal salts, hydrophobic silica and ethylcellulose.

Non-limiting examples of suitable fillers include talc, kaolin, mica, sericite, magnesium carbonate, aluminum silicate and organic powders such as nylon.

Non-limiting examples of suitable dyestuffs include lipophilic dyes, hydrophilic dyes, pigments and mother-of-pearl commonly used in cosmetic or dermatological compositions, and their mixtures.

Non-limiting examples of suitable neutralizers include soda, triethanolamine, aminomethyl propanol and potassium hydroxide.

Non-limiting examples of suitable penetration enhancing agents include alcohols and glycols (ethanol and propylene glycol), ethoxydiglycol, alcohols and fatty acids (oleic acid), fatty acid esters and dimethyl isosorbide.

Non-limiting examples of preservatives compatible with cosmetic and pharmaceutical compositions include benzoic acid, its salts and esters, sorbic acid and its salts, parabens and their salts, triclosan, imidazolidinyl urea, phenoxyethanol, DMDM hydantoin, diazolidinyl urea and chlorphenesin.

Conventionally, the filters are UVA and UVB filters. Non-limiting examples of suitable UVA and UVB filters include organic filters such as benzophenone-3, butyl methoxydibenzoyl methane, octocrylene, octyl methoxycinnamate, 4-methylbenzylidene camphor, octyl salicylate, terephthalylidene dicamphor sulfonic acid and drometrizole trisiloxane, and non-organic filters such as titanium oxide and zinc oxide.

Non-limiting examples of suitable solvents include water, ethanol, glycerin, propylene glycol, butylene glycol and sorbitol.

The quantities of these various additives are those conventionally used in cosmetic and pharmaceutical preparations as is known to a person skilled in the art.

Methods and Uses of the Present Invention

The combination of antioxidant, anti-inflammatory, anti-allergy and metal chelation activities of the short peptides of the present invention render such peptides particularly useful for the treatment of various diseases.

For example, the compositions of the present invention may be useful for the treatment of diseases associated with oxidative stress, diseases associated with the presence or accumulation of advanced glycation end products, diseases associated with the presence or accumulation of metal ions and diseases associated with inflammation and/or allergy. Each possibility represents a separate embodiment of the invention.

In some embodiments, the methods of the present invention comprise administering a composition comprising at least one tetra-peptide of the present invention.

Thus, according to another aspect, the present invention provides a method for treating and/or preventing a disease or disorder associated with at least one of oxidative stress, allergy or inflammation, the method comprising administering to a subject in need a composition comprising a peptide of the present invention or a salt thereof.

According to certain embodiments, the methods comprise administering mixtures of peptides of the invention.

In some embodiments, the present invention provides the use of a peptide of the present invention or a salt thereof for the manufacture of a medicament for the treatment and/or prevention of a disease or disorder associated with at least one of oxidative stress, allergy or inflammation.

In some embodiments, a pharmaceutical composition is provided, comprising a peptide of the present invention or a salt thereof as active ingredient, for use in the treatment and/or prevention of a disease or disorder associated with at least one of oxidative stress, allergy or inflammation.

In some embodiments of the present invention, the relevant diseases or disorders are skin conditions and cosmetic issues.

In some embodiments, the disease or disorder is associated with oxidative stress. Examples of diseases and disorders associated with oxidative stress that may be treated using the peptides of the present invention include, but are not limited to, Alzheimer's disease, Parkinson's disease, diabetes (type I and type II), rheumatoid arthritis, ischemia-reperfusion injury (for example damage to heart and brain tissues) and vitiligo. Each possibility represents a separate embodiment of the invention.

In some exemplary embodiments, the disease is vitiligo. According to these embodiments, a method is provided for treating vitiligo in a subject suffering therefrom, the method comprising applying to the skin of the subject a pharmaceutical composition comprising as active ingredient the peptide of the present invention or a salt thereof.

Vitiligo is a chronic disorder that causes depigmentation of patches of skin due to destruction of melanocytes and/or impairment in melanocytes function. Vitiligo may arise from a number of causes, such as genetic, autoimmune, neurotrophic and toxic factors. In addition, oxidative stress was found to be involved. Handling vitiligo usually include cosmetic camouflage, but the main goal is to stop or slow the progression of pigment loss and, if possible, to return some color to the skin. Current treatments for vitiligo include, for example, application of corticosteroid creams and immunomodulator creams, ultraviolet (UV) light therapy and sometimes melanocyte transplantation by surgery. Such treatments are usually long, cause physical discomfort and associated with a number of adverse effects. Without wishing to be bound by any particular theory or mechanism, it is contemplated that treatment of vitiligo by the method of the present invention involves neutralization of the accumulated hydrogen peroxide by the peptides of the present invention. The method of the present invention thus suggests a safe and efficient treatment for vitiligo.

In some embodiments, the disease or disorder is associated with inflammation. In some embodiments, the disease or disorder associated with inflammation is an auto-immune disease. Examples of diseases and disorders associated with inflammation that may be treated using the peptides of the present invention include, but are not limited to acute inflammation, rheumatoid arthritis, an inflammatory bowel disease and atherosclerosis.

In some embodiments, the disease or disorder is associated with allergy. Examples of diseases and disorders associated with allergy that may be treated using the peptides of the present invention include, but are not limited to, allergic airway disease, allergic rhinitis, eczema, dermatitis, a gastrointestinal food allergy and an ocular allergy.

In some embodiments, the disease is an inflammatory, allergic airway disease (chronic and/or acute flare). In some exemplary embodiments, the disease is asthma. According to these embodiments, a method is provided for treating asthma in a subject, the method comprising administering to the subject a pharmaceutical composition comprising as active ingredient the peptide of the present invention or a salt thereof.

Asthma is a chronic inflammatory disorder of the airways characterized by an associated increase in airway responsiveness to inhaled allergens and nonspecific stimuli. A significant amount of data shows an increase of oxidative stress in allergic airway diseases and indicates a potential role of ROS in pathogenesis of the diseases.

According to another aspect, the present invention provides a method for treating and/or preventing a disease or disorder associated with the presence or accumulation of advanced glycation end products, the method comprising administering to a subject in need thereof a composition comprising as active ingredient a peptide of the present invention or a salt thereof. According to certain embodiments, the method comprises administering mixtures of peptides of the invention.

In some embodiments, the present invention provides the use of a peptide of the present invention or a salt thereof for the manufacture of a medicament for the treatment and/or prevention of a disease or disorder associated with the presence or accumulation of advanced glycation end products.

In some embodiments, a pharmaceutical composition is provided, comprising at least one peptide of the present invention or at least one salt thereof as an active ingredient, for use in the treatment and/or prevention of diseases or disorder associated with the presence or accumulation of advanced glycation end products.

Examples of diseases and disorders associated with advanced glycation end products that may be treated using the peptides of the present invention include, but are not limited to, diabetes (type I and type II), cataract, heart failure, hypertension and callus (such as feet callus).

In some embodiments, the present invention provides the use of a peptide of the present invention or a salt thereof as an anti-inflammatory agent.

In some exemplary embodiments, the present invention provides the use of the peptide Cys-Lys-Met-Cys (SEQ ID NO: 1) as an anti-inflammatory agent. In additional exemplary embodiments, the present invention provides the use of the peptide Cys-Met-Lys-Cys (SEQ ID NO: 2) as an anti-inflammatory agent. In yet additional exemplary embodiments, the present invention provides the use of the peptide Cys-β-Ala-His-Cys (SEQ ID NO: 3), as an anti-inflammatory agent.

In some embodiments, the present invention provides the use of a peptide of the present invention or a salt thereof as an anti-allergic agent.

In some exemplary embodiments, the present invention provides the use of the peptide Cys-Lys-Met-Cys (SEQ ID NO: 1) as an anti-allergic agent. In additional exemplary embodiments, the present invention provides the use of the peptide Cys-Met-Lys-Cys (SEQ ID NO: 2) as an anti-allergic agent. In yet additional exemplary embodiments, the present invention provides the use of the peptide Cys-β-Ala-His-Cys (SEQ ID NO: 3), as an anti-allergic agent.

In some embodiments, the present invention provides the use of a peptide of the present invention or a salt thereof as an anti-oxidant.

In some exemplary embodiments, the present invention provides the use of the peptide Cys-Met-Lys-Cys (SEQ ID NO: 2) as an anti-oxidant. In additional exemplary embodiments, the present invention provides the use of the peptide Cys-β-Ala-His-Cys (SEQ ID NO: 3), as an anti-oxidant.

According to another aspect, the present invention provides a method for treating and/or preventing a disease or disorder associated with the presence or accumulation of metal ions, the method comprising administering to a subject in need thereof a pharmaceutical composition comprising as an active ingredient a peptide of the present invention or a salt thereof.

In some embodiments, the present invention provides the use of a peptide of the present invention or a salt thereof for the manufacture of a medicament for the treatment and/or prevention of a disease or disorder associated with the presence or accumulation of metal ions.

In some embodiments of the present invention, a pharmaceutical composition is provided, comprising at least one peptide of the present invention or at least one salt thereof as an active ingredient, for use in the treatment and/or prevention of a disease or disorder associated with the presence or accumulation of metal ions.

Examples of diseases and disorders associated with the presence or accumulation of metal ions that may be treated using the peptides of the present invention include, but are not limited to, a liver disorder, Alzheimer's disease, heart attack (myocardial infarction), stroke and a prion disease.

The cosmetic industry is constantly looking for new and improved compounds for skin care, particularly for compounds having anti-aging effects. The properties of the peptides of the present invention may be utilized in cosmetic applications, for skin care and protection. For example, the peptides of the present invention may be utilized as anti-aging agents.

Thus, according to yet another aspect, the present invention provides a method for slowing the aging process of the human skin, reducing the signs of aging of the human skin or both, the method comprising applying to the skin a cosmetic composition comprising the peptide of the present invention or a salt thereof.

In some embodiments, slowing the aging process of the human skin and reducing the signs of aging of the human skin encompass improvement of the skin tone, reduction of wrinkles, removal of lines, promotion of skin firmness and reduction of skin sensitivity and irritability.

In some embodiments, a cosmetic composition is provided, comprising a peptide of the present invention or a salt thereof as active ingredient, for use in slowing the aging process of the human skin, reducing the signs of aging of the human skin or both.

In additional embodiments, a cosmetic composition is provided, consisting of a peptide of the present invention or a salt thereof as active ingredient, for use in slowing the aging process of the human skin, reducing the signs of aging of the human skin or both.

The peptides of the present invention may be utilized in the prevention and/or treatment of damages caused by ionizing radiation.

In some exemplary embodiments, the present invention provides the use of the peptide Cys-Lys-Met-Cys (SEQ ID NO: 1) in the prevention or treatment of damages caused by ionizing radiation. In addition exemplary embodiments, the present invention provides the use of the peptide Cys-Met-Lys-Cys (SEQ ID NO: 2) in the prevention or treatment of damages caused by ionizing radiation. In yet additional exemplary embodiments, the present invention provides the use of the peptide Cys-β-Ala-His-Cys (SEQ ID NO: 3) in the prevention or treatment of damages caused by ionizing radiation.

Thus, according to another aspect, the present invention provides a method for the prevention and/or treatment of disorders and harmful effects caused by ionizing radiation, the method comprising administering to a subject in need thereof a composition, comprising a peptide of the present invention or a salt thereof According to one embodiment, the method comprises administering mixtures of peptides of the present invention.

"Ionizing radiations" as used herein include but are not limited to x-rays radiation, alpha radiation, beta radiation, gamma radiation, ultraviolet (UV) radiation, solar radiation, thermal radiation, nuclear radiation, energetic electron radiation, neutron radiation, positron radiation, cosmic radiation, electromagnetic radiation or a combination thereof.

The compositions disclosed herein are also useful in preventing DNA damage which may occur following ionizing radiation exposure. Without wishing to be bound by any theory or mechanism, it has been postulated that UV-B radiation act on DNA through direct excitation process of the nucleobases and further reactions proceed in an oxygen-independent manner. This leads mostly to the formation of dimeric photoproducts at bipyrimidine sites in a strong sequence dependence manner. The photoproducts mostly involve cis-syn cyclobutadipyrimidines (CPDs) and pyrimidine (6-4) pyrimidone photoproducts (6-4 PPs). Most of the damaging effects of UV-A radiation on cellular DNA involve photosensitization reactions.

"Ultraviolet (UV) radiation" is defined herein as a radiation between 10 and 400 nanometers (nm) in wavelength. It is further characterized into ultraviolet A (315-400 nm), B (280-315 nm) and C (100-280 nm). The major source of UV radiation is sunlight, although exposure to artificial sources in the workplace, home and tanning salons are also a risk. Ultraviolet C (UV-C) coming from the sun is usually not harmful since it is screened out by the atmosphere's ozone layer. Although UV-B is an imperative component in the synthesis of vitamin D, it is also responsible for erythema (sunburn) skin cancers and immunosuppression. Ultraviolet A (UV-A) is responsible for skin aging and has additionally been implicated in the development of skin cancers in animals and in immunosuppression in humans. The sun is the main source of UV-A, however use of UV-A lamps for artificial tanning has also been shown to cause adverse side effects. The principal causes of morbidity and mortality attributed to UV radiation are chronic diseases of the skin and the eye however other side effects such as erythema (sunburn), photoaging, photodermatoses, and the formation of nevus, amongst others, are also known (Gllagher and Lee, Prog Biophys Mol Biol. 2006, 92(1)).

The compositions disclosed herein are also useful in treating side effects and disorders associated with UV radiation exposure including cutaneous conditions and ocular diseases linked to UV. Cutaneous conditions include but are not limited to malignant melanoma, basal and squamous cell carcinoma (SCC) of the skin, cancers of the lip, cancers of the pinna (auricle) and non-melanocytic skin cancer (NMSC). Ocular diseases linked to UV radiation exposure include but are not limited to uveal melanoma, cataract, macular degeneration, pterygium and photokeratitis.

According to other embodiments the composition of the present invention may be incorporated into topical sun protecting formulations or sun-protecting compounds, namely any compound capable of blocking or reducing UV-A and/or UV-B radiation exposure to the skin, in order to enhance the effect of the sunblock and/or to reduce or prevent the skin damage. Examples of sun-protecting compounds include sunscreens (conventionally, products with a sun-protecting factor (SPF) of 2 or higher), sunblocks (conventionally, products that physically block radiation exposure and/or have an SPF of 12 or higher), and combinations thereof.

The compositions disclosed herein are also useful in treating ionizing radiation damages which may occur following exposure to radiation in medical procedures performed using medical imaging and medical scanning technologies, directed towards diagnosis or treatment of a disease or a disorder, which may be performed once or multiple times in the same patient. Medical imaging and scanning technologies include but are not limited to angiography, magnetic resonance imaging (MRI), magnetic resonance angiography (MRA), functional magnetic resonance imaging (fMRI), magnetic resonance spectroscopy (MRS), computed tomography (CT), positron emission tomography (PET), positron emission tomography—computed tomography (PET-CT), positron emission tomography—fluorodeoxyglucose (PET-FDG), X-ray, ultrasound, dexa scan (bone D), echocardiography, fluoroscopy, mammography (and R2 image checker), radiolabel scans and nuclear medicine among others.

Medical procedures using imaging and scanning technologies and methods include but are not limited to arthrogram, barium enema, barium swallow, modified barium swallow, hysterosalpinogogram, intra-venous pyelogram (IVP), uterine fibroid embolization (UFE), upper gastrointestinal series (UGI), voiding cystourethrogram (VCUG), aortography, cerebral angiography, coronary angiography, lymphangiography, pulmonary angiography, ventriculography, chest photofluorography, echocardiography, electrical impedance tomography, fluoroscopy, diffuse optical imaging, diffusion-weighted imaging, diffusion tensor imaging, positron emission tomography, scintillography, single photon emission computed tomography (SPECT), gynecologic ultrasonography, obstetric ultrasonography, contrast-enhanced ultrasound, intravascular ultrasound, thermography, virtual colonoscopy and general diagnostic X-ray exams such as abdomen, chest, bones, and spine.

The compositions disclosed herein are also useful in treating and/or preventing side effects and disorders associated with radiation therapy. Common side effects of radiation therapy include but are not limited to bone marrow damage, hair loss, fatigue, skin irritation, soreness in the mouth, throat and esophagus, swelling, infertility and damage to epithelial surfaces such as skin, oral mucosa, pharyngeal, intestine and bowel mucosa, and ureter, all depending on the area of the body which has been treated. Further side effects which can occur months to years after treatment with radiation therapy include but are not limited to fibrosis, epilation (hair loss), lymphedema, heart disease, cognitive decline, radiation proctitis and most common, cancer.

The compositions disclosed herein are also useful in treating and/or preventing side effects and disorders which may occur following diagnosis and/or treatment with nuclear medicine. Nuclear medicine uses radioactive pharmaceuticals that can localize and/or concentrate in specific organs (or tissues) or cellular receptors. Nuclear medicine radioactive pharmaceuticals include but are not limited to calcium-47, carbon-11, carbon-14, chromium-51, cobalt-57, cobalt-58, erbium-169, fluorine-18, gallium-67, gallium-68, hydrogen-3, indium-111, iodine-123, iodine-125, iodine-131, iron-159, krypton-81m, nirrogen-13, oxygen-15, phosphorus-32, samarium-153, selenium-75, sodium-22, sodium-24, strontium-89, thallium-201, xenon-133, yttrium-90 and technetium-99m.

Workers and people living in the vicinity of a nuclear plant, medical staff of clinics and laboratories using specific technologies and materials, astronauts, pilots and aircrafts crews are constantly exposed to varying doses of ionizing radiation. Hence, the compositions disclosed herein are also useful in treating and/or preventing side effects and disorders which may occur following chronic or one time exposure to nuclear radiation or other ionizing radiations. Furthermore, the compositions of the present invention are useful in treating and/or preventing side effects and disorders which may occur following exposure to nuclear radiation of nuclear and radiation accidents or the use of nuclear weapon.

The compositions disclosed herein are also useful in treating and/or preventing adverse effects and disorders associated with the use of contrast agents (also known as medical contrast medium) in diagnostic and therapeutic medical procedures such as many kinds of imaging and scanning. An exemplary disorder associated with the use of iodinated contrast agents includes contrast-induced acute kidney injury (CI-AKI) (also known as contrast-induced nephropathy).

Diagnostic and therapeutic medical imaging procedures which use contrast agents include, but are not limited to, angiography, percutaneous coronary intervention, venography, voiding cystourethrography (VCUG), hysterosalpingogram (HSG), intravenous urography (IVU), barium enema, double contrast barium enema (DCBE), barium swallow, barium meal, double contrast barium meal, barium follow through, virtual colonoscopy, contrast-enhanced CT, contrast-enhanced MRI, dynamic contrast-enhanced MRI and contrast-enhanced ultrasound (CEUS).

Contrast agents include, but are not limited to, radiocontrast agents, iodine, iodinated contrast agents, diatrizoate, metrizoate, ioxaglate, iopamidol, iohexol, ioxilan, iopromide, iodixanol, barium, barium sulfate, thorotrast, gadodiamide, gadobenic acid, gadopentetic acid, gadoteridol, gadofosveset, gadoversetamide, gadoxetic acid, gadobutrol, gadocoletic acid, gadodenterate, gadomelitol, gadopenamide, gadoteric acid, cliavist, combidex, endorem (feridex), resovist, sinerem, perflubron, optison, levovist, microbubble contrast agents, gadolinium-containing contrast agents, iron-oxide contrast agents, Mn-DPDP and natural products such as blueberry and green tea.

According to other embodiments the composition is administered within 24 hours before the exposure to the ionizing radiation or at about the time of exposure to the ionizing radiation and/or within 24 hours after the exposure to the ionizing radiation. The pharmaceutical composition may be administered in one or more doses within 24 hours before the radiation exposure or in one or more doses at about the time of the radiation exposure and/or in one or more doses within 24 hours after the radiation exposure. According to alternative embodiments the composition is administered in one or more doses within 12 hours, within six hours or within three hours or less before and/or after the exposure to the ionizing radiation.

According to other embodiments the composition of the present invention is administered one or more times before the radiation exposure and one or more times after the radiation exposure. According to other embodiments the composition may be administered one or more times within 24 hours prior to the radiation exposure for example at about 1, 6, 12, 18 or 24 hours prior to the radiation exposure and further administered one or more times within 24 hours after the radiation exposure, for example at about 1, 6, 12, 18 or 24 hours after the radiation exposure.

The amount of the pharmaceutical or cosmetic composition of the present invention to be administered for the above indications, the administration regimes as well as their mode of application will depend both on characteristics of the treated individual (age, size, gender, etc.) as well as on parameters associated with the phenomena to be treated.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Peptide Synthesis

The following new five peptides were synthesized by Solid Phase Peptide Synthesis (SPSS) using Fmoc strategy (all five peptides were >98% pure):

N-acetyl-Cys-Lys-Met-Cys-NH$_2$, designated herein as DY-65 (SEQ ID NO: 4);

N-acetyl-Cys-βAla-His-Cys-NH$_2$, designated herein as DY-66 (SEQ ID NO: 6);

N-acetyl-CysγGlu-Cys-NH$_2$, designated herein as DY-67 (SEQ ID NO: 13);

N-acetyl-Cys-Met-Lys-Cys-NH$_2$, designated herein as DY-70 (SEQ ID NO: 5); and

N-acetyl-Cys-γGlu-Cys-Cys-NH$_2$, designated herein as DY-71(SEQ ID NO: 12).

The peptides were prepared by SPSS in which there were repeated cycles of coupling-deprotection. The first stage of the technique consisted of peptide chain assembly with protected amino acid derivatives on a polymeric support. The second stage of the technique was the cleavage of the peptide from the resin support with the concurrent cleavage of all side chain protecting groups to give the crude free peptide.

The free N-terminal amine of a solid-phase attached peptide was first coupled to a single N-protected amino acid unit. This unit was then deprotected, revealing a new N-terminal amine to which a further amino acid was attached. After cleavage from the resin, peptides were then purified by reverse phase HPLC using columns.

Fmoc deprotection: 0.08 mmol of Fmoc-X-Wang resin was loaded into a fritted column equipped with a plastic cap. The resin was washed twice with 3 mL portions of dimethylformamide (DMF) for 1 minute each. Next, 3 ml of 20% piperidine in DMF was added and deprotection allowed to continue for 15 minutes. During this time, the column was gently swirled in order to assure a complete mixing. After the reaction was complete (in about 15 minutes), the reaction column was drained and the resin washed 4 times with 3 mL of DMF.

Amide bond coupling: In a small vial, 3 equivalents of the Fmoc amino acid was preactivated by combining it with equal equivalents of O-Benzotriazole-N,N,N',N'-tetramethyl-uronium-hexafluoro-phosphate (HBTU), 6 equivalents of DIPEA (N,N'-diisopropylethylamine), and 3 mL of DMF. This solution was fully dissolved and then allowed to react for an additional 3-5 minutes. Then this coupling solution was added to the resin. The cap was placed on the reaction column and the resin slurry agitated every 2-3 minutes over a period of 20 minutes.

Cleavage: In order to obtain the peptide in the free acid form, the ester linkage was cleaved using trifluoroacetic acid (TFA). The resin was treated with 2-3 mL of a solution of TFA and water in a ratio of 95:5. The resin was then agitated over a period of 25 minutes. The column was subsequently drained and the filtrated collected into a glass collection vessel. The material was then dried in diethyl ether and analyzed.

In addition, the following peptides, known as CB3 and CB4, were also synthesized by SPSS using Fmoc strategy:

CB3:
(SEQ ID NO: 14)
N-acetyl-Cys-Pro-Cys-NH$_2$

CB4:
(SEQ ID NO: 15)
N-acetyl-Cys-Gly-Pro-Cys-NH$_2$

Example 2

Effect of the Peptides on Carrageenan-Induced Hind-Paw Swelling

The above new five peptides were examined for anti-inflammatory activity, and their activity was compared to that of peptide CB3. Male ICR mice received an i.p. administration of each of the tested peptide (150 mg/kg) 30 min prior to the injection of carrageenan into the sub-plantar area of both of the animal's hind paws. Carrageenan was dissolved in water at concentration of 3 mg/ml and injected at a volume of 50 µl. Hind paw thickness was measured by Mitutoyo® micrometer before carrageenan injection and afterward at intervals of 1 hour between each measurement. Swelling was calculated as the difference between the thickness of the hind paw measured at each time interval and its size at time 0 (before carrageenan injection). n=6 foot pads (3 animals) for each group.

As can be seen in FIG. 1, the most active peptide was DY-65, which showed swelling reduction of 40%, 27% and 34% after 1, 2, and 3 hours, respectively, compared to control (saline only). Reduced swelling compared to control was also observed for DY-66, DY-67, and to a lesser extent for DY-70 and DY-71. CB3 did not show a significant reduction compared to control.

Example 3

Effect of the Peptides on Lipid Peroxidation in the Lung in a Murine Model of Zymosan-Induced Inflammation Zymosan-induced shock. Male BALB/c mice were randomly allocated into the following experimental groups (8 mice for each group):

(1) Zymosan+vehicle group ("ZYM"). Mice were treated intraperitoneally with zymosan 500 mg/kg.

(2) Zymosan+DY-66 group ("ZYM+DY-66"). Identical to the Zymosan+vehicle group but peptide DY-66 was administered.

(3) Zymosan+DY-65 group ("ZYM+DY-65"). Identical to the Zymosan+vehicle group but peptide DY-65 was administered.

(4) Zymosan+DY-70 group ("ZYM+DY-70"). Identical to the Zymosan+vehicle group but peptide DY-70 was administered.

(5) Zymosan+DY-71 group ("ZYM+DY-71"). Identical to the Zymosan+vehicle group but peptide DY-71 was administered.

(6) Zymosan+DY-67 group ("ZYM+DY-67"). Identical to the Zymosan+vehicle group but peptide DY-67 was administered.

(7) Sham group ("Sham"). Identical to the Zymosan+vehicle group but a vehicle was administered instead of zymosan.

The peptides were administered by an intraperitoneal (i.p.) route of administration as follows:

The first dose (50 mg per kg) was given 3 days before the zymosan injection.
The second dose (50 mg per kg) was given 2 days before the zymosan injection.
The third dose (50 mg per kg) was given 1 day before the zymosan injection.
The fourth dose (120 mg per kg) was given 30 minutes before the zymosan injection.
The fifth dose (120 mg per kg) was given 5 hours after the zymosan injection.

The peptides were formulated in D5W (5% dextrose in water, "D5W"). The vehicle control was D5W. At 24 hours after administration of zymosan, animals were euthanized and assessed for inflammation by an MDA (malondialdehyde) analysis of lung tissue. All the materials and drugs (apart from the peptides) were obtained from Sigma, Inc.

Determination of MDA activity. Malondialdehyde (MDA) formation was used to quantify lipid peroxidation, measured as thiobarbituric acid-reactive material. Tissues were homogenized (100 mg/mL) in 1.15% KCl buffer and homogenates (200 mL) were then added to a reaction mixture consisting of 0.75 mL 0.8% thiobarbituric acid, 100 mL 8.1% (volume per volume) sodium dodecyl sulfate, 0.75 mL 20% (v/v) acetic acid (pH 3.5) and 300 mL $dH_2O$, and heated at 95° C. for 60 min. After cooling to room temperature, samples were cleared by centrifugation at 10,000 g for 10 min and absorbance was measured at 532 nM using 1,1,3,3-tetramethoxypropane as an external standard. The level of lipid peroxides was expressed as nM MDA/mg protein.

Data analysis. All values in FIG. 2 and the text below were expressed as mean ±standard deviation (SD) and standard error (SE) of n observations. For the in vivo studies n represents the number of animals studied. The results were analyzed by one-way ANOVA followed by a Bonferroni's post-hoc test for multiple comparisons. A p-value of less than 0.05 was considered significant.

Figure 2:
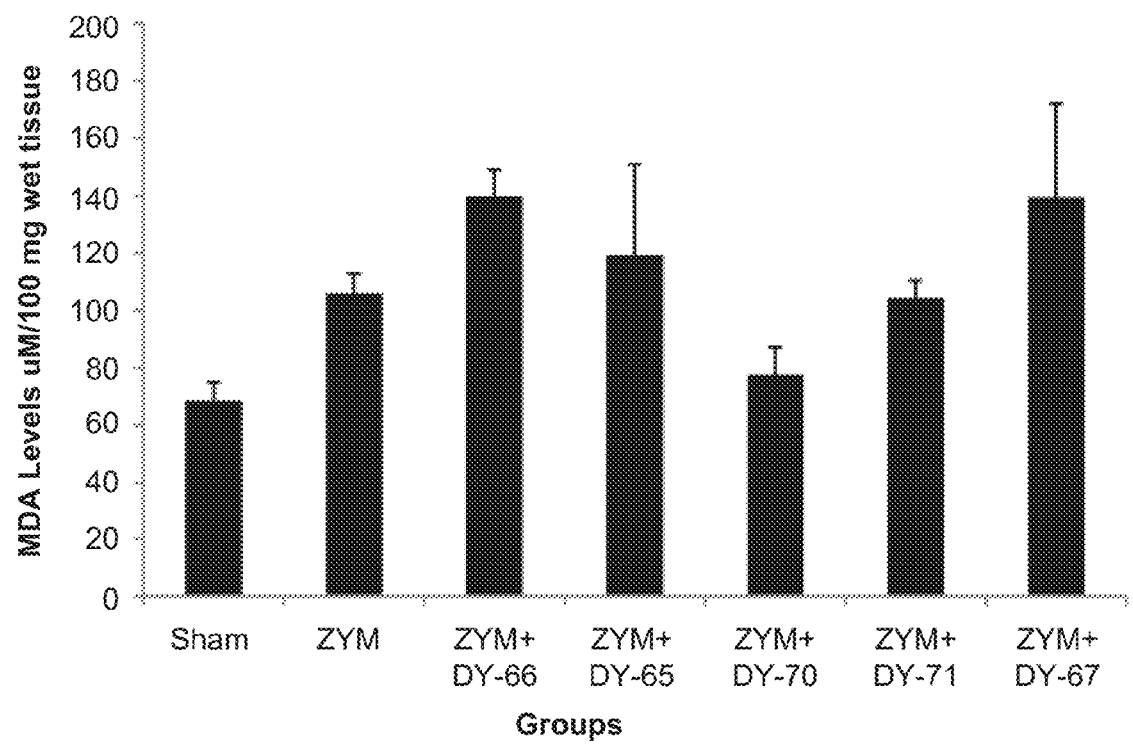
FIG. 2. Effect of peptides on malondialdehyde (MDA) activity.
Figure 3A:
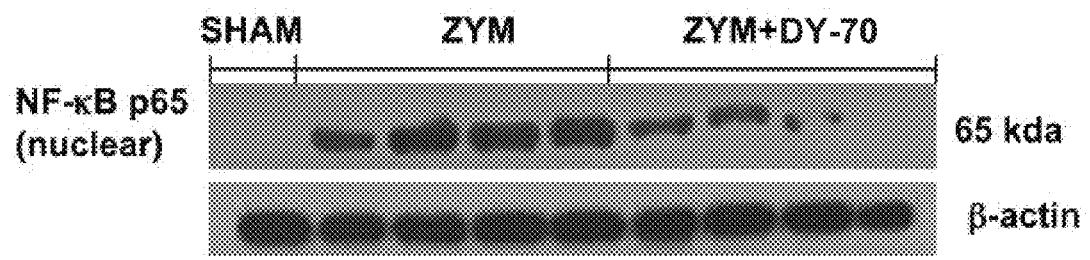
FIG. 3A-F. Effect of the peptides on nuclear translocation of NF-κB and cytoplasmic stability of I-kappaBalpha. The gels show representation of 4 samples. The densitometry results reflect all samples (up to 8 samples for each peptide).
Figure 3B:
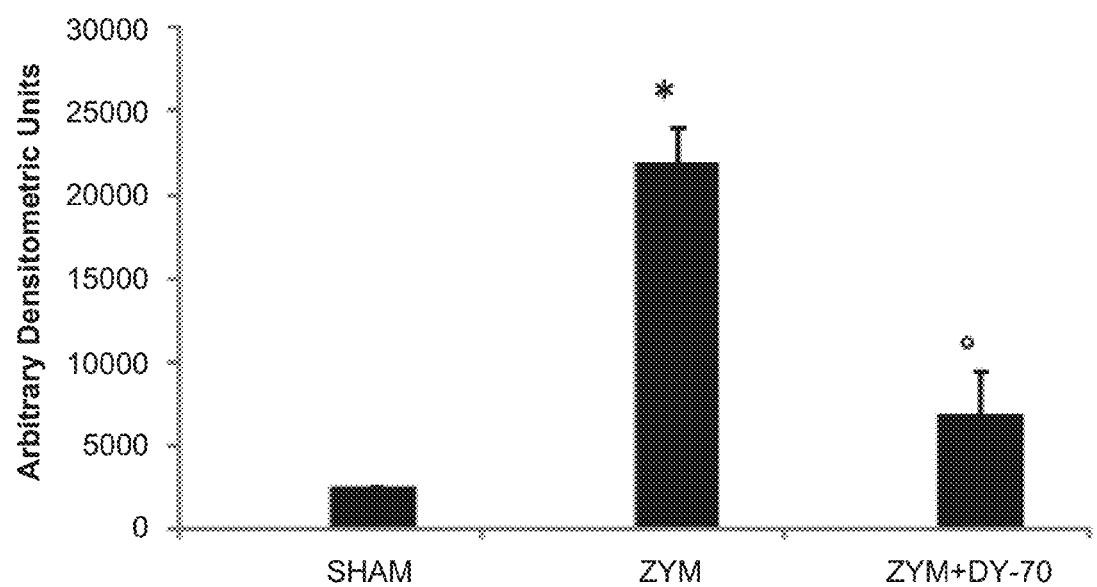
Figure 3C:
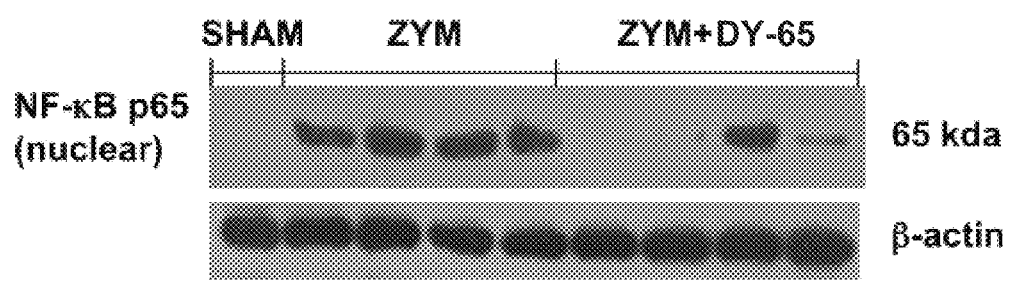
Figure 3D:
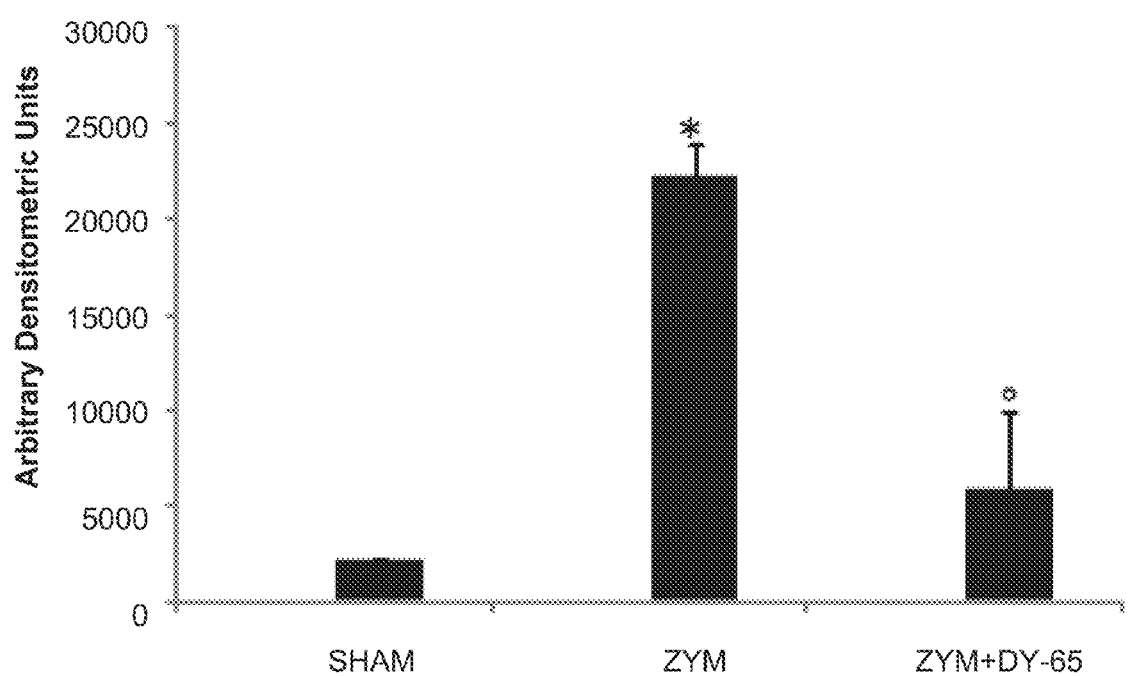
Figure 3E:
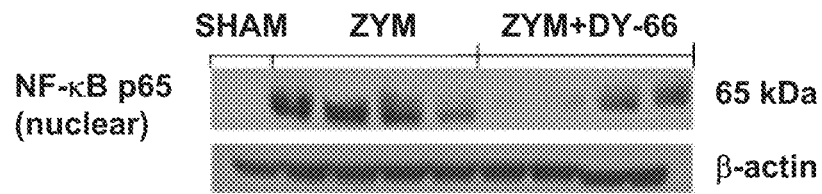
Figure 3F:
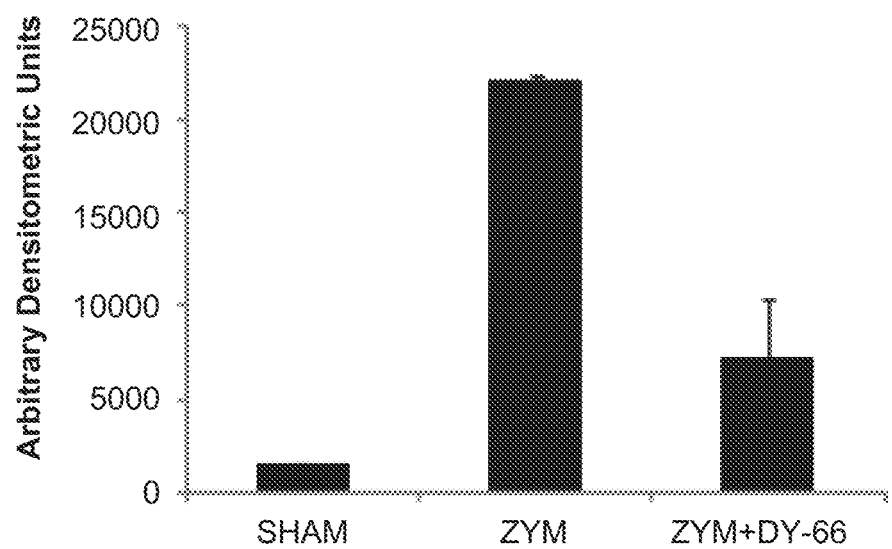

Effect of the peptides on MDA activity. As can be seen in FIG. 2, zymosan administration induced a 50% increase in MDA activity in the lung tissue at 24 hours after zymosan administration. Treatment with peptide DY-70 inhibited the elevation in MDA concentration in the lung tissue ($p<0.05$).

Example 4

Effect of the Peptides on Nuclear Translocation of NF-kappaB and Cytoplasmic Stability of I-kappa-Balpha in the Lung in a Murine Model of Zymosan-Induced Inflammation The following peptides were examined in this Example: DY-65, DY-66 and DY-70.

Zymosan-induced shock. Male BALB/c mice were randomly allocated into the following experimental groups:

(1) Zymosan+vehicle group ("ZYM"). Mice were treated intraperitoneally with zymosan 500 mg/kg.

(2) Zymosan+DY-65 group ("ZYM+DY-65"). Identical to the Zymosan+vehicle group but peptide DY-65 was administered.

(3) Zymosan+DY-66 group ("ZYM+DY-66"). Identical to the Zymosan+vehicle group but peptide DY-66 was administered.

(4) Zymosan+DY-70 group ("ZYM+DY-70"). Identical to the Zymosan+vehicle group but peptide DY-70 was administered.

(5) Sham group ("SHAM"). Identical to the Zymosan+vehicle group but a vehicle was administered instead of zymosan.

The peptides were administered by an intraperitoneal (i.p.) route of administration as described in Example 3.

The peptides were formulated in D5W as described in Example 3. The vehicle control was D5W.

At 24 hours after administration of zymosan, animals were euthanized and assessed for inflammation by an NF-κB analysis of lung tissue.

Determination of nuclear translocation of NF-κ B. Tissues were homogenized and nuclear extracts prepared via centrifugation. ELISA for p50 was performed, using a series of standards in order to define absolute concentrations.

Determination of cytoplasmic stability of I-κBalpha. Tissues were homogenized and nuclear extracts prepared via centrifugation. ELISA for IkappaBalpha was performed, using a series of standards in order to define absolute concentrations.

Data analysis. All values in FIG. 3 and the text below were expressed as mean ±standard deviation (SD) and standard error (SE) of n observations. For the in vivo studies n represents the number of animals studied. The results were analyzed by one-way ANOVA followed by a Bonferroni's post-hoc test for multiple comparisons. A p-value of less than 0.05 was considered significant.

Effect of the peptides on nuclear translocation of NF-κ B. As can be seen in FIG. 3A-F, Zymosan ("ZYM") administration induced a 10-fold increase in p65 nuclear translocation in the lung tissue at 24 hours after zymosan administration. Treatment with peptide DY-65 or DY-70 inhibited the increase in nuclear p65 translocation by >80% (p<0.05). Treatment with peptide DY-66 inhibited the increase in nuclear p65 translocation by ca. 80% (p<0.05).

Effect of peptides on cytoplasmic stability of I-kappaBalpha. Zymosan administration induced a 4-fold decrease in cytoplasmic IkappaBalpha concentration in the lung tissue at 24 hours after zymosan administration. Treatment with peptides DY-65, DY-66 or DY-70 inhibited the decrease in cytoplasmic IkappaBalpha concentrations by >50-80% (p<0.05 for all three peptides), with efficacy of DY-70>DY-65>DY-66.

Example 5

Reversal of Oxidative Stress-Induced Phosphorylation of p38 and JNK by the New Peptides All five peptides were examined in this Example according to the following procedure:

Cell Culture and Treatment:

Human neuroblastoma SH-SY5Y cells were maintained in Dulbecco's modified Eagle's medium (DMEM, Invitrogen) supplemented with 10% fetal bovine serum (Invitrogen), 100 µg/ml streptomycin and 100 U/ml penicillin G (Gibco). Cells were plated at a density of $6.25 \times 10^4/cm^2$ and incubated for 24 hours, after which they were exposed to different treatments.

Cell Viability:

SH-SY5Y cells were plated on 96-well plates and treated with Auranofin (AuF) (5 µM) for 30 min. Then the cells were washed with PBS and treated with either one of the peptides at the indicated concentrations. Twenty-four hours later, the cells were fixed with glutaraldehyde in final concentration of 0.5% for 10 min. Cells were washed 3 times with DDW dried over night, and washed once with borate buffer (0.1M, pH 8.5). The fixed cells were stained with 200 µl of 1% methylene blue dissolved in borate buffer for 1 hour. After extensive washing and drying, the color was extracted with 200 µl of 0.1 M HCl for 1 h at 37° C. and absorbance was read in spectrophotometer at 630 nm.

Western Blot Analysis and Antibodies:

Twenty to thirty micrograms of protein samples were loaded on 10-12% SDS-PAGE gels. The proteins were then transferred electrophoretically to nitrocellulose (Whatman, Germany). The blots were blocked by incubation for 1 h at room temperature (RT) in TBS-T (25 mM Tris-HCl pH 7.4, 0.9% NaCl and 0.02% Tween-20) with 4% Difco skim milk (BD, USA), and incubated over-night at 4° C. with the primary antibody: pERK½ (Thr 202/Tyr204), mouse mAb, (1:6,000); p-SAPK/JNK (Thr183/Tyr185), rabbit mAb; SAPK/JNK, mouse mAb; p-p38MAP Kinase (Thr180/Tyr182), rabbit mAb; cleaved caspase 3, rabbit mAb. All antibodies were from Cell Signaling Tech. USA, used at 1:1000. Purified b Catenin, mouse mAb, (1:10,000; BD Transduction Laboratories, USA) diluted in 5% BSA, 0.04% Azide in TBS-T. Proteins were detected with Anti-Mouse or Anti-Rabbit IgG-HRP linked antibody (1:10,000; Cell Signaling, Tech. USA).

The results are summarized in Table 1 hereinbelow. As can be seen from the table, all five peptides were highly effective in reducing phosphorylation of p38 MAP Kinase and JNK (c-Jun N-terminal kinases) at concentrations in the range of 20-90 µM. DY-70 and DY-65 were the most potent.

TABLE 1

Inhibition of MAPK phosphorylation by the peptides

| Compound | JNK phosphorylation ($IC_{50}$) µM | p38 phosphorylation ($IC_{50}$) µM |
|---|---|---|
| DY-65 | 32.3 | 36.7 |
| DY-66 | 86.9 | 67.0 |
| DY-67 | 67.3 | 36.5 |
| DY-70 | 22.1 | 22.2 |
| DY-71 | 82.3 | 46.9 |

Example 6

Effect of the Peptides on Ovalbumin-Induced Hypersensitivity in Mice—Analysis of Blood and Peritoneal Exudates Samples The following peptides were examined in this Example: DY-65, DY-66 and DY-70.

Hypersensitivity. Male BALB/c mice (6-8 weeks old) were housed under specific pathogen-free conditions and maintained on a 12-hour light/dark cycle, with food and water ad libitum. All materials and drugs were obtained from Sigma, Inc.

Mice in Groups A, B, C, and E (n=10 per group) were sensitized with intraperitoneal (i.p.) 200 µl of sterile PBS containing 100 µg ovalbumin (OVA) and 1.6 mg alum on days 0 and 7, and challenged with intraperitoneal (i.p.) 200 µl of sterile PBS containing 10 µg ovalbumin (OVA) on day 14 in order to induce an experimental model of allergic peritonitis. Mice in Group F (n=10) were injected with intraperitoneal (i.p) 200 µl sterile PBS ("sham" group, no OVA and no Alum).

Mice in Groups A, B, and C, were treated with 150 µl of sterile PBS containing peptides DY-66, DY-65 and DY-70, respectively, at a dose of 125 mg/kg on days 13, 14, and 15 via an i.p. route of administration.

Mice in Groups E and F were treated with 150 µl of sterile PBS on days 13, 14, and 15 via an i.p. route of administration. On day 14 the test articles (or PBS vehicle) were injected 30 minutes before injecting the OVA.

Blood taken on day 16 was tested for 1) serum anti-OVA IgE, 2) white blood cell count and differential (including absolute and percentage of eosinophils count). Serum was frozen at −80° C. for future optional blood tests.

Data analysis. All values in FIG. 4 and the text below were expressed as mean ±standard deviation (SD) and standard error (SE) of n observations. For the in vivo studies n represents the number of animals studied. The results were analyzed by one-way ANOVA followed by a Bonferroni's post-hoc test for multiple comparisons. A p-value of less than 0.05 was considered significant.

Figure 4A:
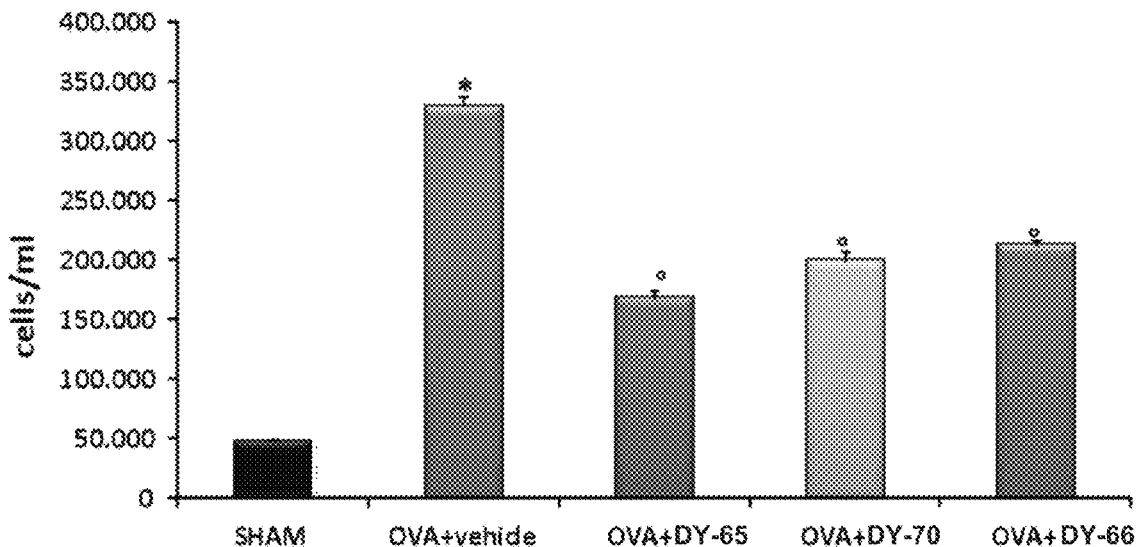
FIG. 4A-C. Effect of peptides on ovalbumin-induced hypersensitivity in mice—analysis of blood and peritoneal exudates samples.
Figure 4B:
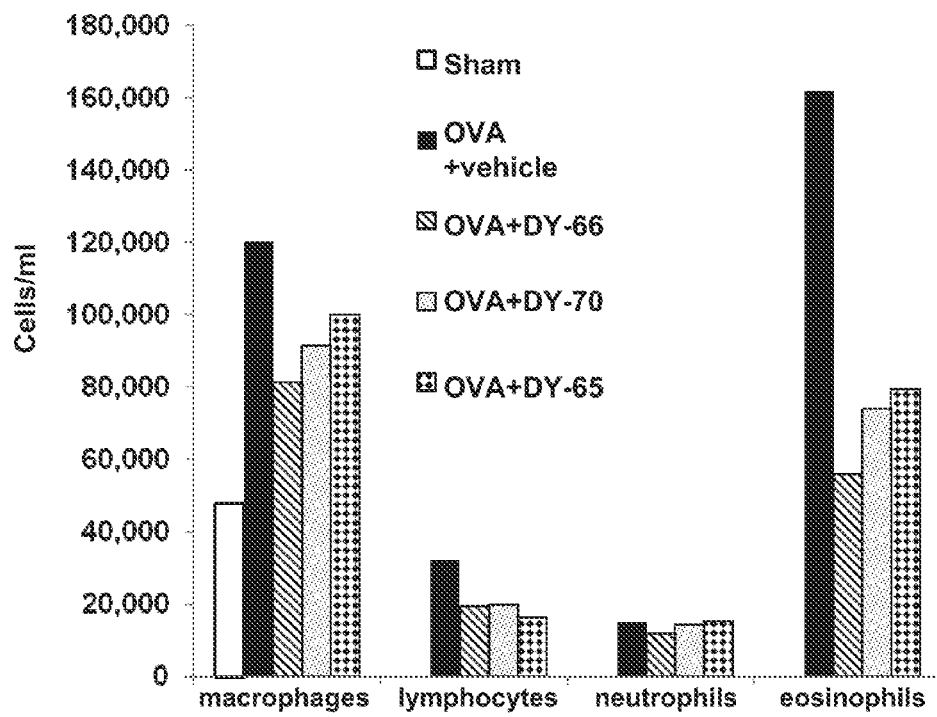

Effect of peptides on peritoneal cellularity. As can be seen in FIG. 4A, OVA immunization ("Ova+vehicle") induced a nearly 7-fold increase in the cellularity of the peritoneal exudates. All three peptides significantly reduced the elevation in this cellularity, as follows: DY-65>DY-70>DY-66. The effect on macrophage and eosinophil cellularity in the peritoneal exudate followed the same rank ordering (FIG. 4B).

Figure 4C:
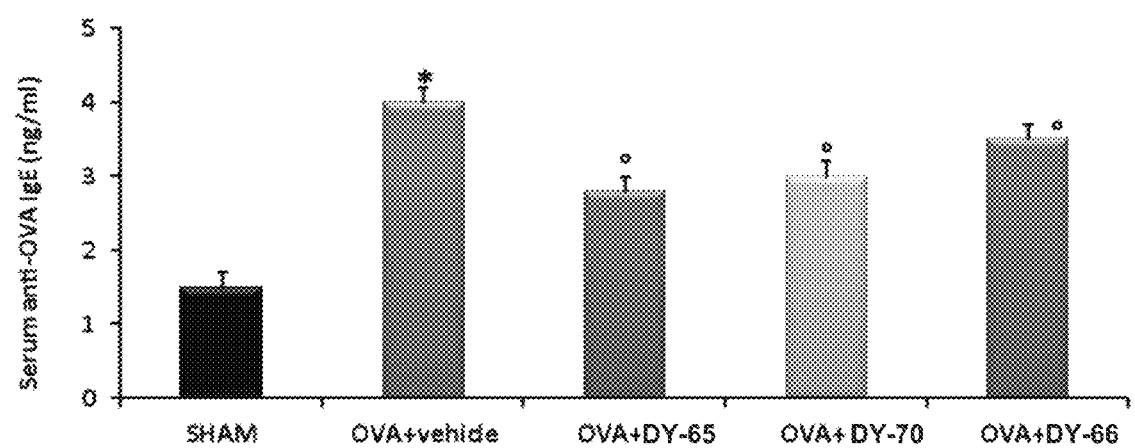

Effect of peptides on serum anti-OVA IgE levels. As can be seen in FIG. 4C, OVA immunization induced a nearly 2.5-fold increase in the titer of anti-OVA serum IgE. All three peptides significantly reduced the elevation in this titer, as follows: DY-65>DY-70>DY-66, with the greatest reduction ca. 60% of the OVA-induced elevation.

Example 7

Effect of the Peptides on Ovalbumin-Induced Hypersensitivity in Mice—Analysis of Peritoneal Exudate Samples In this example, peptide DY-66 was examined and compared to the known CB3 peptide.

Hypersensitivity was induced as described in Example 5. The mice were treated according to the above protocol with PBS alone ("PBS", no OVA and no Alum), OVA ("OVA"), OVA+CB3 104 mg/kg, OVA+DY-66 83 mg/kg and OVA+DY-66 125 mg/kg. In all groups, 9 mice were used except for OVA+DY-66 83 mg/kg, where 10 mice were used.

At day 16 the animals were sacrificed, the peritoneum was washed with 4-5ml of sterile PBS, centrifuged and the cells were re-suspended in sterile PBS containing FCS 2%.

Figure 5A:
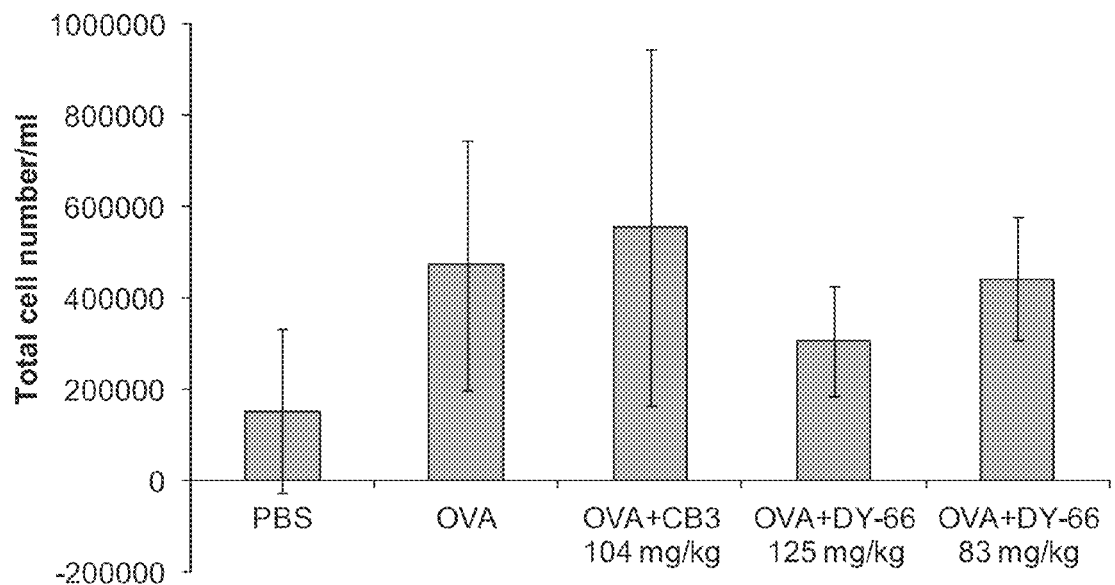
FIG. 5A-H. Effect of peptides on ovalbumin-induced hypersensitivity in mice—analysis of peritoneal exudate samples.
Figure 5B:
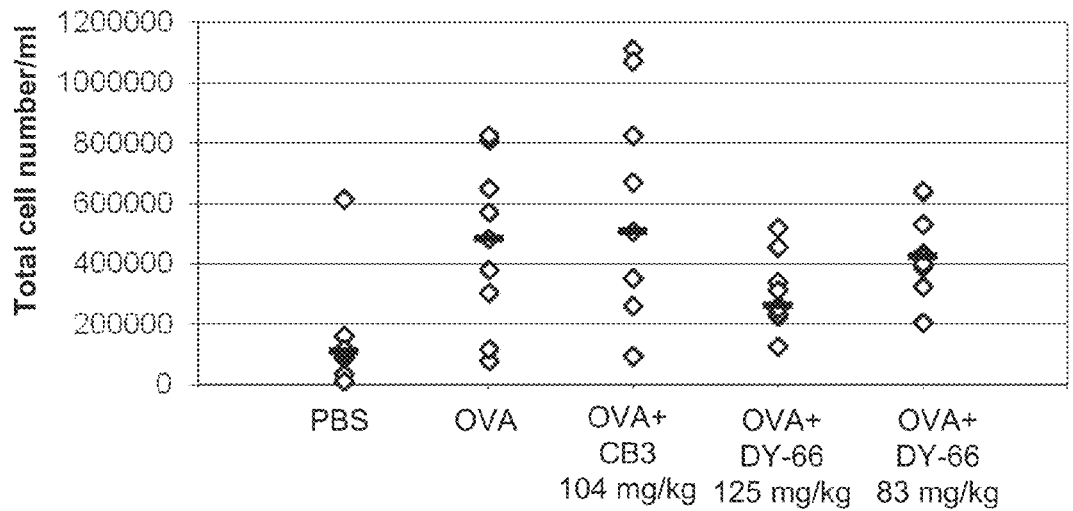

Total white blood cells (WBC) counts. Total WBC were collected by peritoneal washing (where needed, red blood cells, RBC, were lysed) and analyzed by FACS machine to count total cell numbers during 10 seconds flow. Averages and STDEV are shown in FIG. 5A. All results+medians are shown in FIG. 5B. Medians are marked by horizontal lines.

Figure 5C:
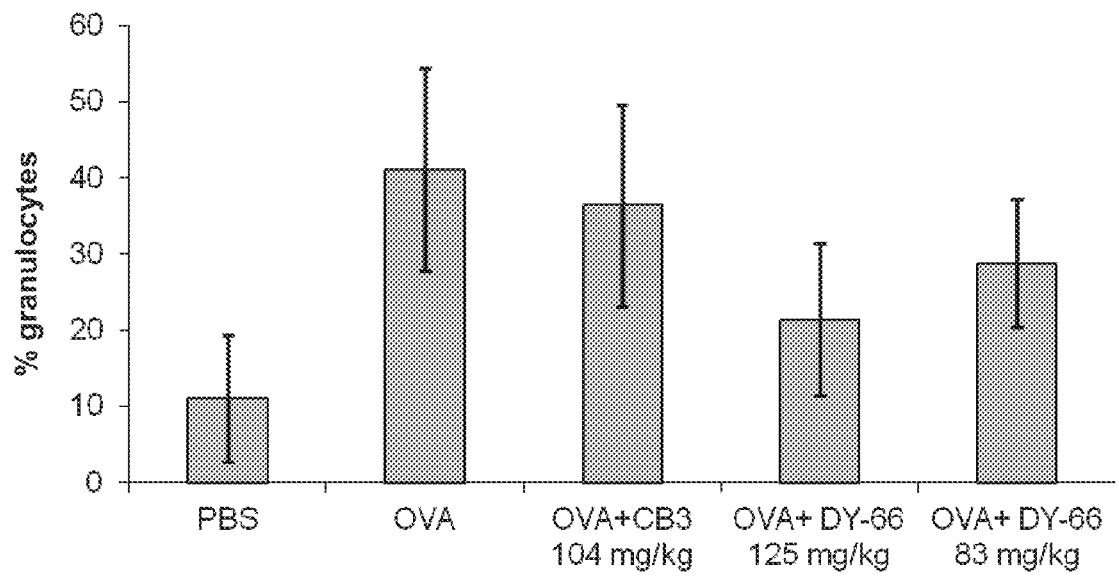
Figure 5D:
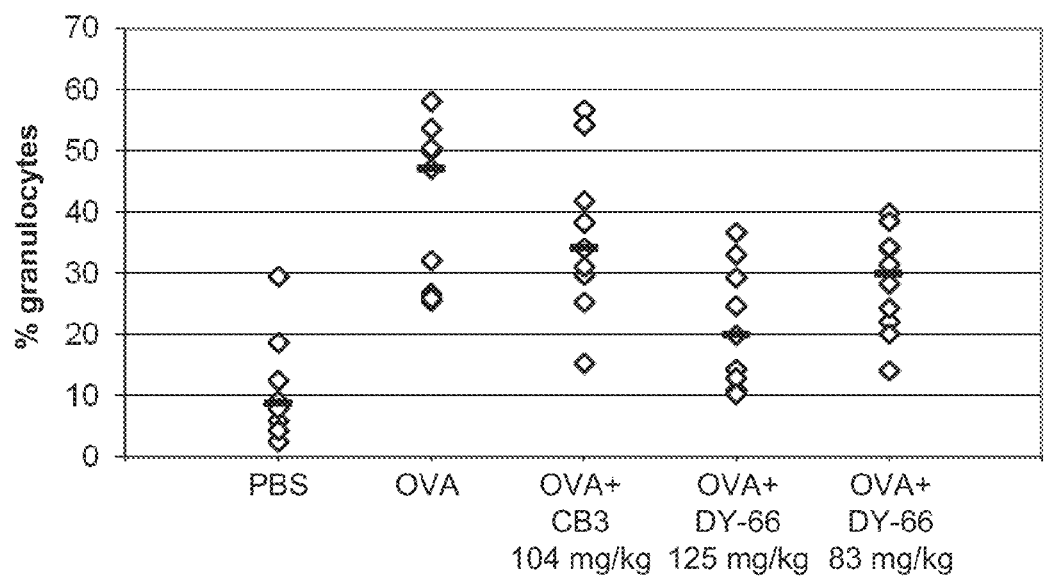

Percentage of total granulocytes. Percentage of granulocytes at the peritoneal lavages were measured by the use of FACS machine analysis of all cells during 10 second flow, followed by a careful analysis of the FACS dot plots. Averages+STDEV are shown in FIG. 5C, and all results+medians are shown in FIG. 5D. Except for the difference between PBS and OVA that was found significant, also the difference between medians of OVA and OVA+DY-66 125 mg/kg was found to be highly significant, according to Mann-Whitney test+the stringent correction of Bonfferoni ($p<=0.0125$ (0.05/4)).

Figure 5E:
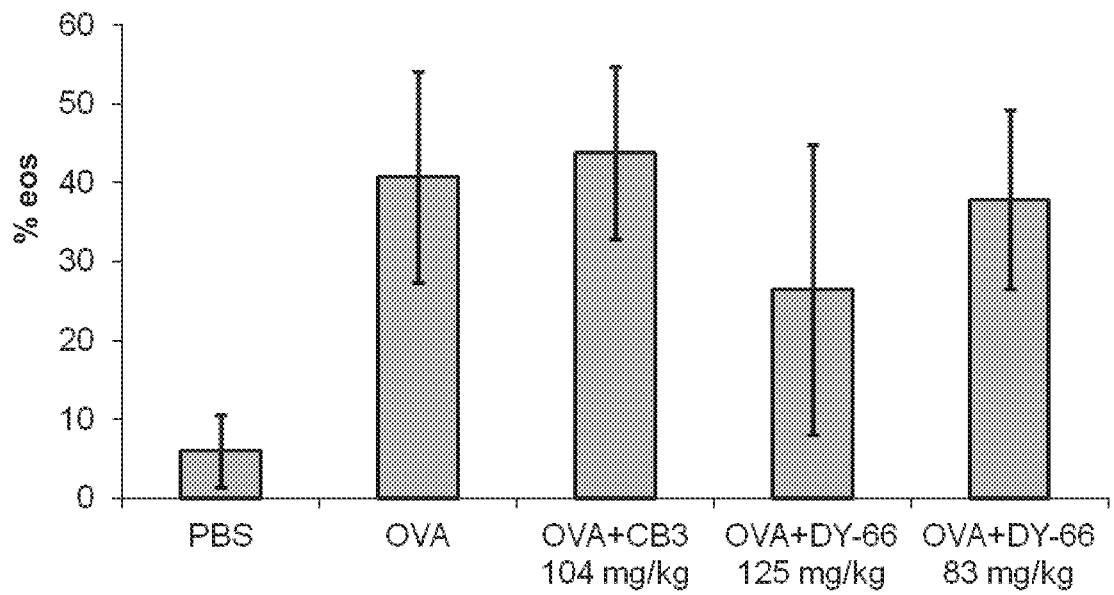
Figure 5F:
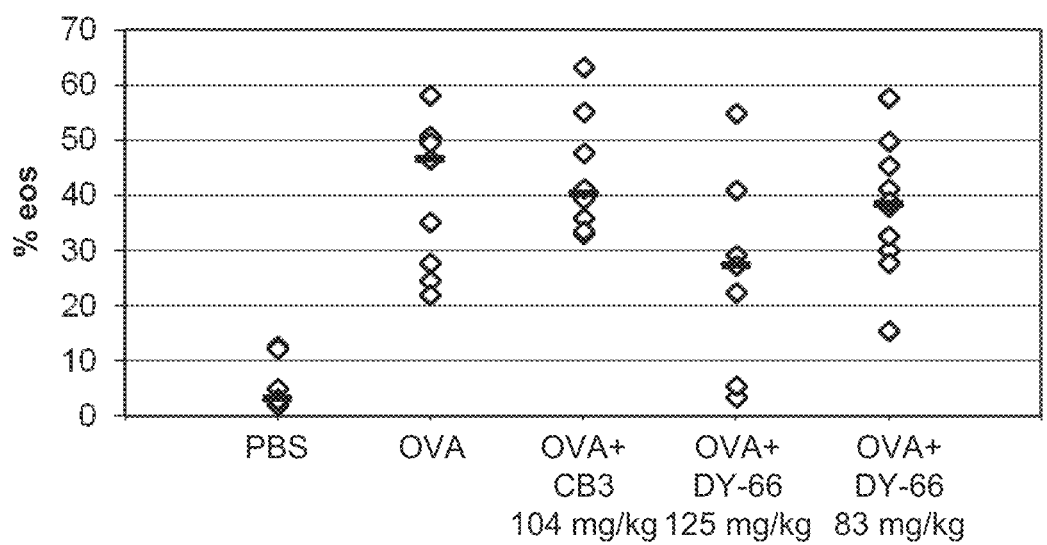

Eosinophil (Eos.) percentage About 100,000 cells were taken from each sample and "blotted" on a slide by the use of a cytospin machine. Slides were stained with "Wright-Giemsa" stain solution for identification of eosinophils, mast cells, other WBC and RBC. Cells were counted and % of eos was calculated. Averages and STDEV are shown in FIG. 5E. All results+medians are shown in FIG. 5F. Medians are marked by horizontal lines.

Figure 5G:
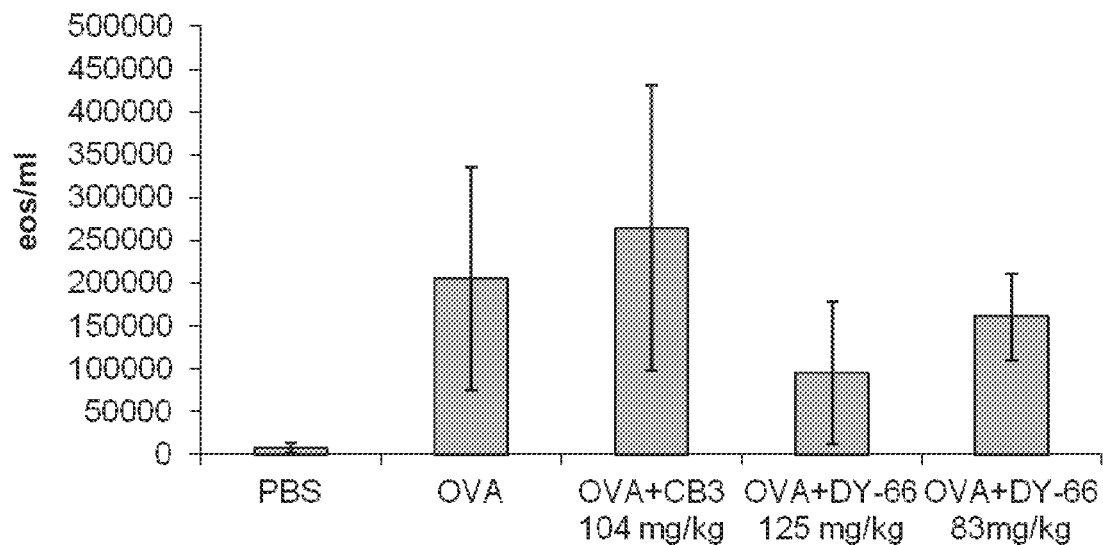
Figure 5H:
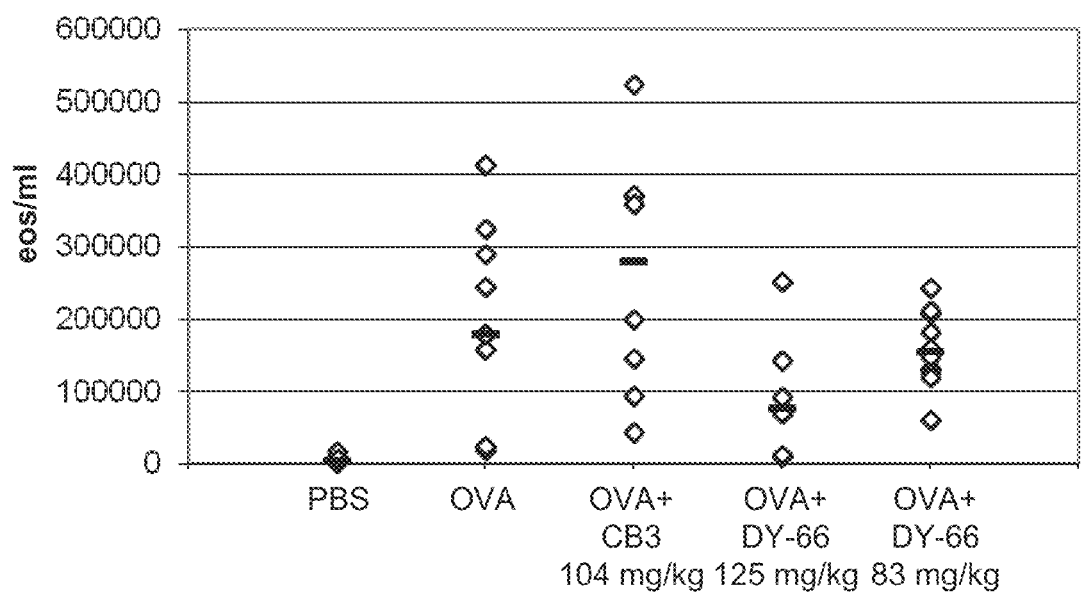

Absolute numbers of eos/ml. Total eos. numbers were calculated by multiplying total WBC counts by eos. % (divided by 100). Averages and STDEV are shown in FIG. 5G. All results and medians are shown in FIG. 5H. Medians are marked by horizontal lines.

Example 8

Effect of the Peptides on Hydrogen Peroxide-Induced HaCat Keratinocyte Cytotoxicity All five peptides were examined in this Example, and their activity was compared to the known CB3 peptide. HaCaT cells were seeded in 96-well plate at a concentration of $10 \times 10^4$ cells/ml for 24 hours. Then cells were incubated with the peptides at the indicated concentrations for 2.5 hours followed by washing with PBS and incubation with 90 µM hydrogen peroxide (without peptide) for 30 minutes. Cells were washed with PBS and incubated with culture medium containing peptide for 72 hours. Cell viability was tested by MTT. The effect of the peptides on cell viability was performed similarly without hydrogen peroxide exposure.

The results are summarized in FIG. 6. "Control HaCaT"—cells that were neither treated by peptide nor by hydrogen peroxide; "Medium"—well without cells that contained only culture medium; "HaCaT $H_2O_2$"—cells treated with hydrogen peroxide.

Figure 6A:
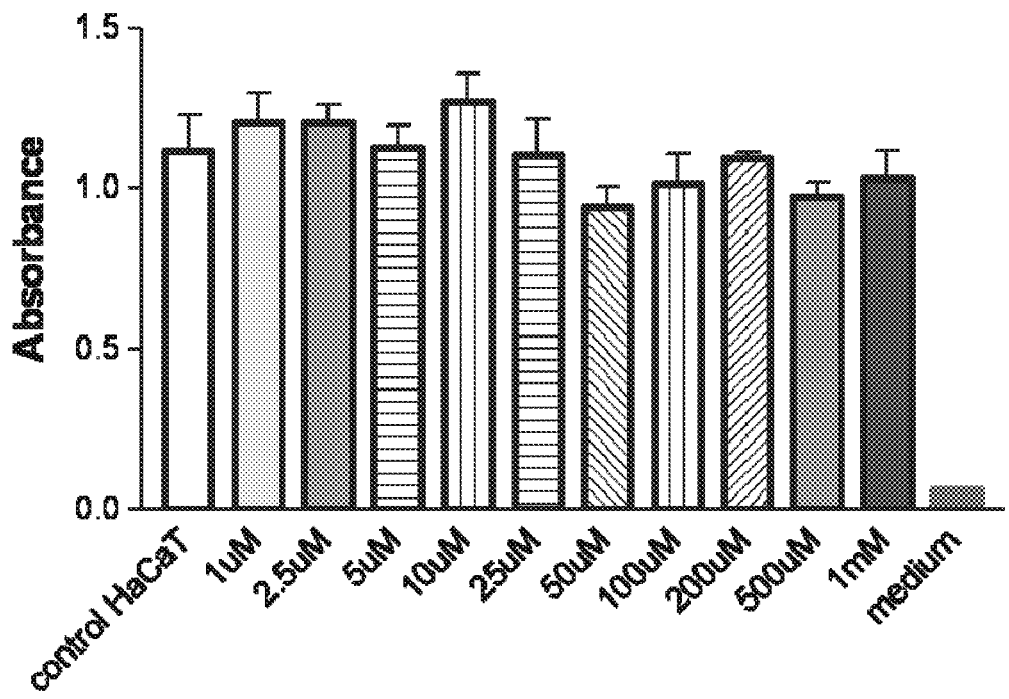
FIG. 6A-D. Effect of peptides on hydrogen peroxide-induced HaCaT keratinocyte cytotoxicity. 6A, C—effect of the tested peptide on HaCaT cell viability (no hydrogen peroxide). 6B, D—effect of the tested peptide on hydrogen peroxide-induced cytotoxicity in HaCaT cells.
Figure 6B:
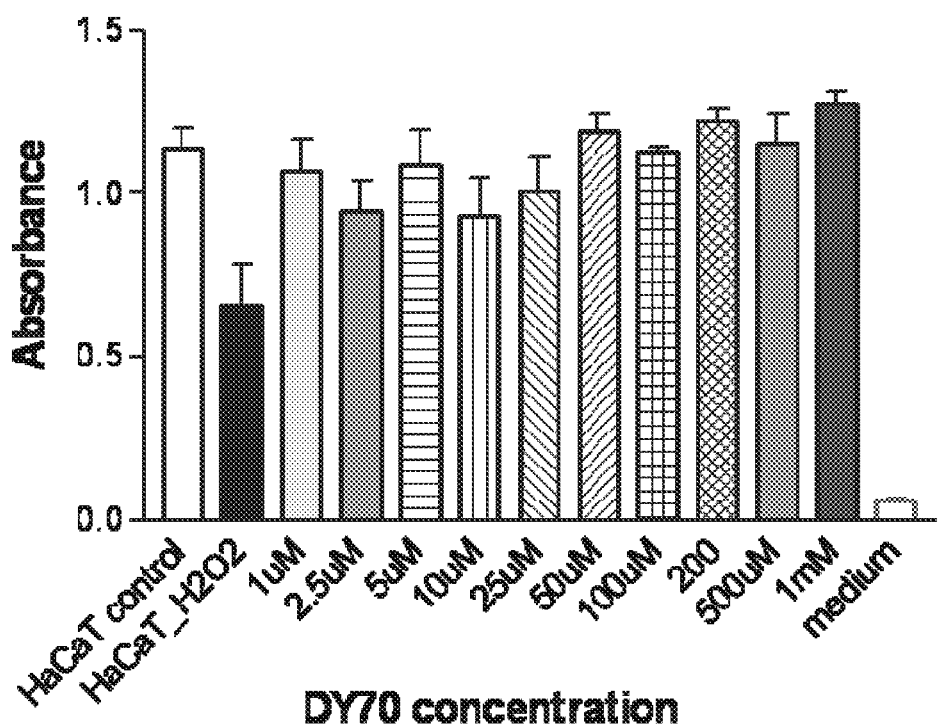
Figure 6C:
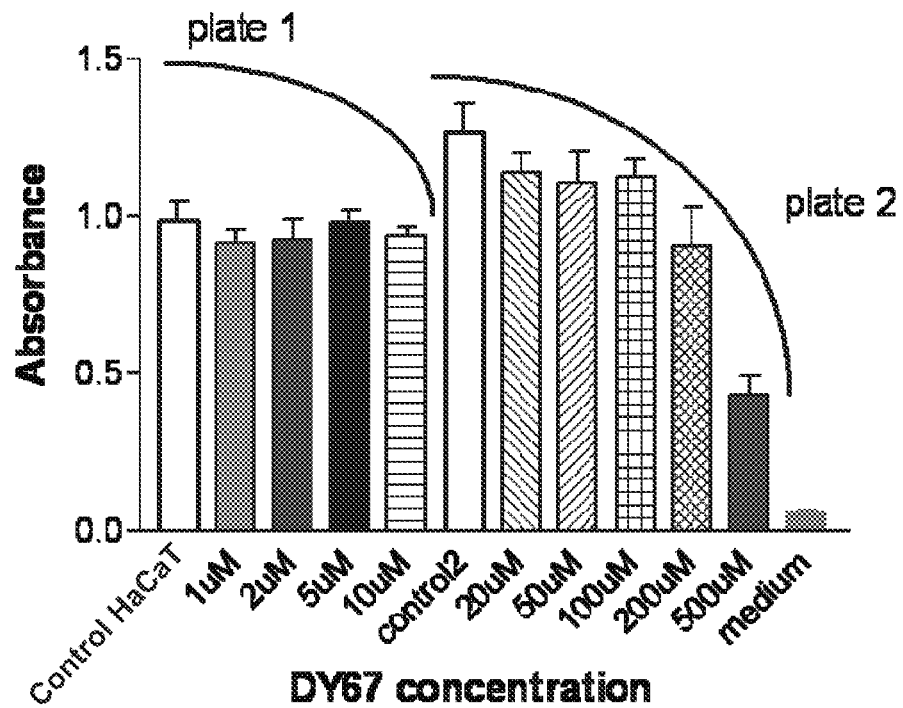
Figure 6D:
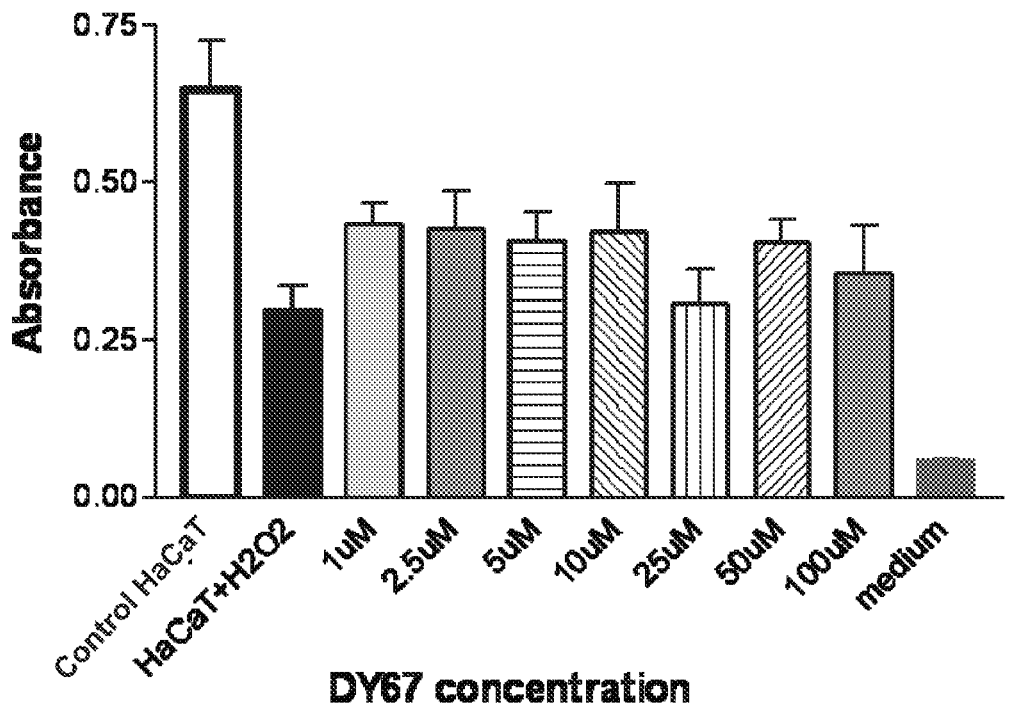

The results have shown that peptide DY-70 fully protected the cells from hydrogen peroxide at all tested concentrations (FIGS. 6A—no hydrogen peroxide; 6B—after hydrogen peroxide exposure). Peptide DY-67 caused increase of about 45% in cell viability at concentrations of 1-10 µM (FIGS. 6C-no hydrogen peroxide; 6D—after hydrogen peroxide exposure). Peptides DY-65, DY-66, DY-71 and CB3 slightly elevated cell viability at selected concentrations after hydrogen peroxide exposure.

Example 9

Effect of DY-65 on Carnitine Levels in Mouse Tissues

Male ICR mice were injected i.p. with 250 mg/kg DY-65 for 5 consecutive days. Half an hour after the last injection lung, heart, skeletal muscle (femural), brain, liver, kidney and blood were removed, homogenized (100 mg tissue in 200 µl distilled water), centrifuged and filtrated through 30K Microcon® filter. Carnitine analysis was carried out by a commercial kit (BioVision, catalogue number K642-100). n=4 for each group.

The results have shown a significant elevation (about 150% increase) in the level of carnitine in some tissues. In other tissues, an elevation in the level of carnitine was observed (about 70% increase). The results were verified in pooled tissues, as well as in individual animals.

Example 10

Effect of the Peptides on UVB-Induced Cell Cytotoxicity in HaCaT Cells

The following peptides were examined in this Example and their activity was compared to the known CB3 peptide: DY-65, DY-66 and DY-70.

HaCaT cells were seeded in 96-wells plate ($10 \times 10^4$/ml) and incubated in 37° C., 6% $CO_2$ for 24 hours. Cells were incubated with the peptides at the indicated concentrations for 2.5 hours and washed (PBS). Then 100 µl PBS were added to each well followed by UVB irradiation (0.05J/ cm²). Cells were washed with PBS and incubated with culture medium (DMEM, 100 μl) containing the peptides. MTT assay was carried out after 72 hours.

Figure 7A:
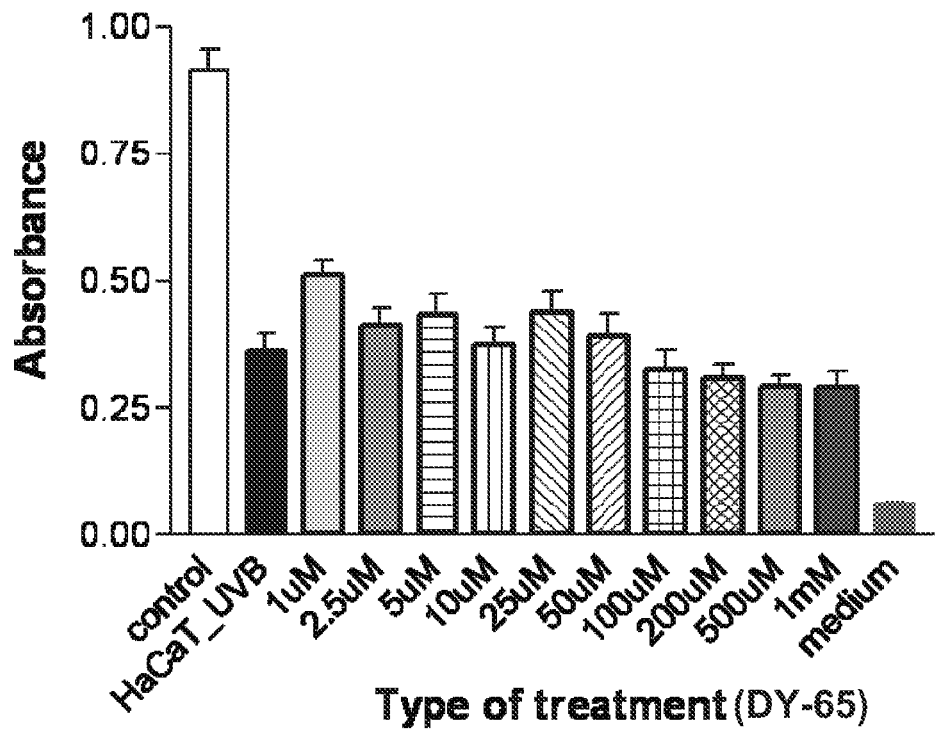
FIG. 7A-C. Effect of the peptides on UVB-induced cell cytotoxicity in HaCaT cells.
Figure 7B:
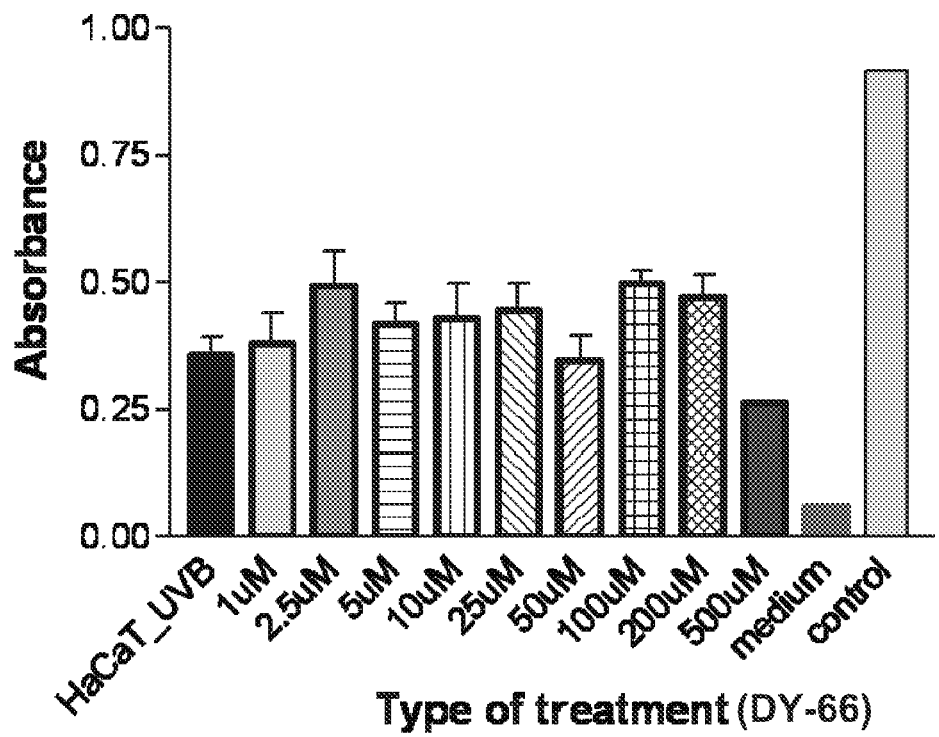
Figure 7C:
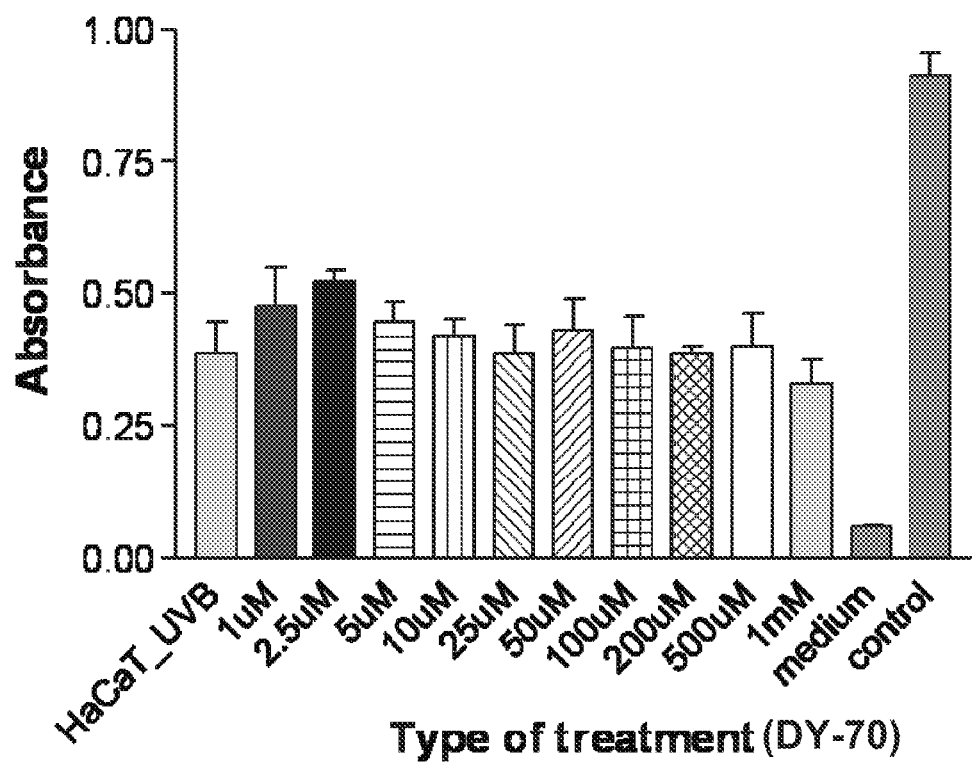

The results are summarized in FIGS. 7A-C. "Control"—cells that were neither treated by peptide nor by UVB irradiation; "Medium"—well without cells that contained only culture medium; "HaCaT UVB"—cells treated with UVB irradiation.

The results have shown that peptides DY-65 (FIG. 7A), DY-66 (FIG. 7B) and DY-70 (FIG. 7C) showed protective effect at low concentrations.

Example 11

Effect of DY-66 on ROS Levels in C57Bl/6 Mice after Lipopolysaccharide (LPS) Injection C57BL/6 female mice (7-8 weeks old) were injected i.p. with the peptide or PBS on days -3, -2, -1 at a dose of 50 mg/kg or with PBS alone (6 mice in each group). On day zero all the mice were injected i.p. with 200 μg/mouse of LPS and 45 min. later they were injected i.p. with 150 mg/kg of the peptide. Another group of 3 mice served as normal untreated mice. Six hours after LPS injection mice were bled into heparinized tubes (approx. 300 μl of blood from each mouse) and the level of ROS was measured in the plasma.

The results have shown a significant reduction in ROS levels in platelets and RBCs of mice treated with peptide DY-66 compared to PBS-treated mice.

Platelets: ROS level in DY-66-treated mice was approximately 55% of the level measured in PBS-treated mice ($p<0.005$).

RBCs: ROS level in DY-66-treated mice was approximately 75% of the level measured in PBS-treated mice ($p<0.05$).

Example 12

Effect of the Peptides on Liver Inflammation in C57BL/6 Mice

First, all five peptides were examined in a mouse model of liver inflammation induced by injection (i.v.) of Concanavalin A (Con-A).

Six groups of C57BL/6 female mice (7-8 weeks old) containing 6 mice in each group were injected i.p. with different peptide on days -3, -2, -1 at a dose of 50 mg/kg or with PBS alone. On day zero all the mice were injected i.v. with 250 μg/mouse of Con A and 45 min. later they were injected i.p. with 150 mg/kg of each peptide or PBS.

Eight hours after Con A injection mice were bled into heparinized tubes (approx. 150 ul of blood from each mouse) and the levels of alanine aminotransferase (ALT) was measured in the plasma.

One day later the mice were sacrificed and their livers were placed in 4% formalin and sent for pathological examination.

Administration of Con A induced a dramatic increase in ALT levels. Peptide DY-66 reduced ALT average by 69% and ALT median was reduced by 75% compared to PBS-treated mice. In addition, treatment with DY-66 resulted in significant ($p=0.011$) decrease in necrotic area according to histo-pathological report.

Although the mice were injected with sub-lethal dose of Con A (250 μg/20 g), 24 hours post Con A injection 3 mice of the PBS treated group and 1 mouse of the DY-65 treated mice were found dead. There were no mortalities in the other groups. This suggests that most of the peptides had some beneficial effect over Con A induced liver inflammation.

Next, peptide DY-66 was examined and compared to N-acetylcysteine (NAC), CB3 and CB4. The compounds were tested according to the procedure described above. ConA dose was 180 μg/mouse.

Figure 8:
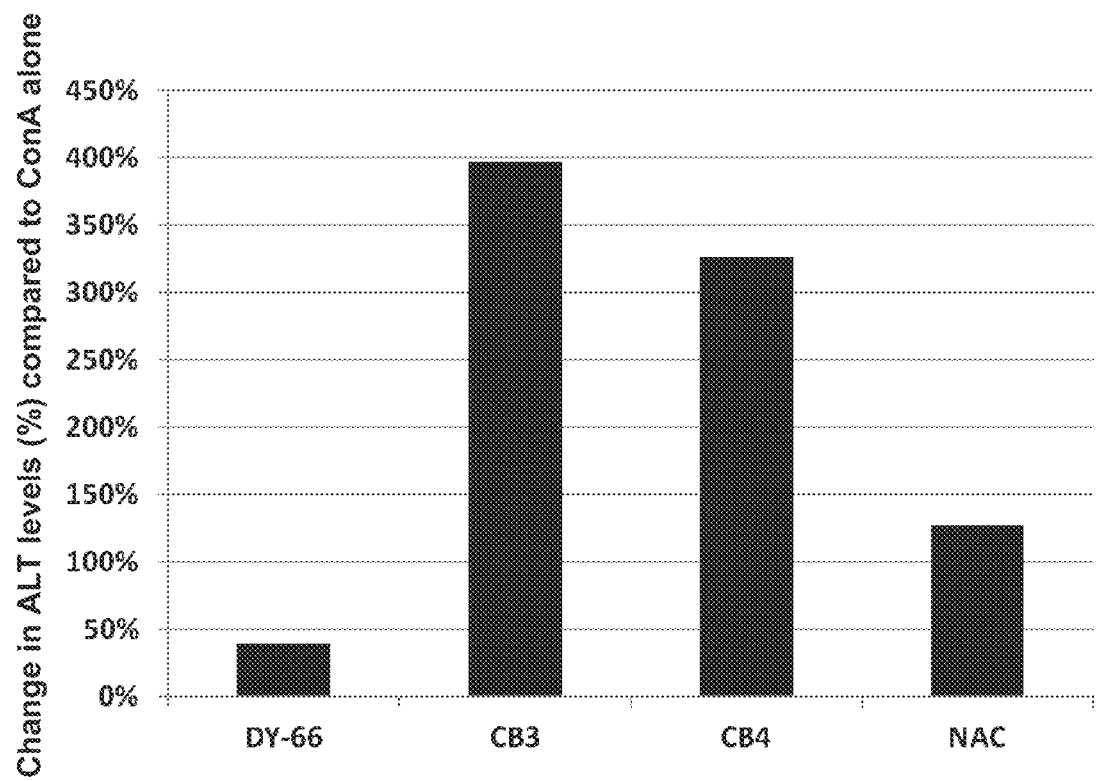
FIG. 8. Effect of DY-66 on liver inflammation in a mouse model of liver inflammation induced by injection (i.v.) of Concanavalin A (Con-A).

FIG. 8 presents the change in ALT levels (%) for each of the tested compounds compared to PBS treatment (i.e., the ratio between ALT levels in samples obtained from mice treated with a tested compound and ALT levels in samples obtained from PBS-treated mice)

Peptide DY-66 reduced ALT average by 71% and ALT median was reduced by 89% compared to PBS-treated mice. Both CB3 and CB4 resulted in highly increased ALT level compared to PBS-treated mice. NAC did not induce a significant change in ALT level compared to PBS-treated mice.

Example 13

Metal Chelation

All five peptides were examined for their ability to bind copper and ferric ions. 0.83 mM of each peptide were mixed with 1.66 mM of either $FeCL_3$ or $CuSO_4$. The mixtures were incubated for 1 hour at room temperature and further kept at° 4 C until analysis. Samples were analyzed by mass spectra (ESI).

Cupper binding was observed for DY-65, DY-66 (low degree) and DY-70 (low degree). FeCl binding was observed for DY-66 and DY-70 (low degree).

Example 14

Effect of Peptide on the Level of Advanced Glycation End-Products

Scope of work: establish the in vitro efficacy of a tested peptide (for example, DY-66) in suppressing development of advanced glycation end products in endothelial cells incubated in a high glucose medium.

Bovine aortic endothelial cells are cultured for 7 days in MEM with 30 mM glucose and 0.4% fetal bovine serum, with daily change of media. These conditions have been previously shown to induce a 261% increase in the concentration of advanced glycation end products.

Prior to exposure to 30 mM glucose, cells are randomly allocated to the following experimental groups:
  1. Sham (5 mM glucose; no exposure to 30 mM glucose)
  2. Vehicle control (30 mM glucose)
  3. Peptide (40, 100, or 400 μM)+30 mM glucose
  4. Carnosine (40, 100, or 400 μM)+30 mM glucose
  5. N-acetylcysteine (NAC) (40, 100, or 400 μM)+30 mM glucose Each condition is represented in triplicate. Given 10 conditions, and 3 replicates per condition, a total of 30 wells are incubated.

After 7 days of incubation, cells are harvested and cytosol extracted for dot-blot analysis of immunoreactive AGE using a commercially-available monoclonal antibody.

Blots are developed and densitometry performed. The IC50's of the tested peptide and carnosine are determined and expressed as mean±standard error.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A synthetic peptide selected from the group consisting of:

Cys-Lys-Met-Cys (SEQ ID NO: 1), and
Cys-Met-Lys-Cys (SEQ ID NO: 2),
wherein the synthetic peptide is a tetra-peptide, and wherein the synthetic peptide is in the form of a salt.

2. The synthetic peptide of claim 1, wherein the salt is selected from the group consisting of trifluoroacetic acid (TFA), acetate and citrate.

3. The synthetic peptide of claim 1, further comprising a permeability-enhancing moiety selected from the group consisting of lipids, fatty acids, steroids and bulky aromatic or aliphatic compounds.

4. The synthetic peptide of claim 3, wherein the permeability-enhancing moiety is a fatty acid.

5. The synthetic peptide of claim 4, wherein the fatty acid is selected from the group consisting of palmitic acid, phosphatidic acid, stearic acid, arachidonic acid, docosahexaenoic acid, eicosapentaenoic acid and oleic acid.

6. A composition comprising a synthetic peptide according to claim 1.

7. The composition of claim 6, wherein the composition is formulated as a pharmaceutical composition and further comprises a pharmaceutically acceptable diluent, excipient or carrier; or as a cosmetic composition and further comprises a cosmetically acceptable diluent, excipient or carrier.

8. The composition of claim 7, wherein the composition is formulated for topical administration or for systemic administration.

9. A method for treating a disease or disorder associated with oxidative stress, the method comprising administering to a subject in need thereof a pharmaceutical composition comprising as active ingredient a synthetic peptide according to claim 1, wherein the disease or disorder associated with oxidative stress is selected from the group consisting of Alzheimer's diseases, Parkinson's disease, diabetes, rheumatoid arthritis, ischemia-reperfusion injury and vitiligo.

10. A method for treating a disease or disorder associated with inflammation, the method comprising administering to a subject in need thereof a pharmaceutical composition comprising as active ingredient a synthetic peptide according to claim 1, wherein the disease or disorder associated with inflammation is selected from the group consisting of acute inflammation, rheumatoid arthritis and atherosclerosis.

11. A method for treating a disease or disorder associated with allergy, the method comprising administering to a subject in need thereof a pharmaceutical composition comprising as active ingredient a synthetic peptide according to claim 1, wherein the disease or disorder associated with allergy is selected from the group consisting of an allergic airway disease, allergic rhinitis, eczema, dermatitis, a gastrointestinal food allergy and an ocular allergy.

12. A method for treating a disease or disorder associated with the presence or accumulation of advanced glycation end products, the method comprising administering to a subject in need thereof a pharmaceutical composition comprising as active ingredient a synthetic peptide according to claim 1, wherein the disease or disorder associated with the presence or accumulation of advanced glycation end products is selected from the group consisting of diabetes, cataract, hypertension and callused skin.

13. A method for slowing the aging process of the human skin, reducing the signs of aging of the human skin or both, the method comprises applying to the skin a cosmetic composition comprising as active ingredient a synthetic peptide according to claim 1.

14. A method for treating harmful effects or disorders caused by ionizing radiation comprising administering to a subject in need thereof a composition comprising as active ingredient a synthetic peptide according to claim 1, wherein the harmful effects or disorders caused by ionizing radiation is a coetaneous condition selected from the group consisting of malignant melanoma, basal and squamous cell carcinoma (SCC) of the skin, lip cancer, cancer of the auricle and non-melanocytic skin cancer (NMSC), or an ocular disease selected from the group consisting of uveal melanoma, cataract, macular degeneration, pterygium and photokeratitis.

* * * * *

```
                         SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Cys Lys Met Cys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Cys Met Lys Cys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X= beta-alanine

<400> SEQUENCE: 3

Cys Xaa His Cys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (4)..(4)
<223> OTHER INFORMATION: C-terminal amide group

<400> SEQUENCE: 4

Cys Lys Met Cys
1

<210> SEQ ID NO 5
<211> LENGTH: 4
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (4)..(4)
<223> OTHER INFORMATION: C-terminal amide group

<400> SEQUENCE: 5

Cys Met Lys Cys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (2)..(2)
<223> OTHER INFORMATION: X= beta-alanine
<220> FEATURE:
<221> NAME/KEY: MISC_FEATURE
<222> LOCATION: (4)..(4)
<223> OTHER INFORMATION: C-terminal amide group

<400> SEQUENCE: 6

Cys Xaa His Cys
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X= gamma-glutamyl

<400> SEQUENCE: 7

Cys Xaa Cys Cys
1

<210> SEQ ID NO 8
<211> LENGTH: 3
<212> TYPE: PRT
<213> ORGANISM: Artificial Sequence
<220> FEATURE:
<223> OTHER INFORMATION: Synthetic peptides
<220> FEATURE:
<221> NAME/KEY: MISC_FEATURE
<222> LOCATION: (2)..(2)
<223> OTHER INFORMATION: X= gamma-glutamyl

<400> SEQUENCE: 8

Cys Xaa Cys
1

<210> SEQ ID NO 9
<211> LENGTH: 4
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification
<220> FEATURE:
<221> NAME/KEY: MISC_FEATURE
<222> LOCATION: (4)..(4)
<223> OTHER INFORMATION: C-terminal modification

<400> SEQUENCE: 9

Cys Lys Met Cys
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification
<220> FEATURE:
<221> NAME/KEY: MISC_FEATURE
<222> LOCATION: (4)..(4)
<223> OTHER INFORMATION: C-terminal modification

<400> SEQUENCE: 10

Cys Met Lys Cys
1

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification
<220> FEATURE:
<221> NAME/KEY: MISC_FEATURE
<222> LOCATION: (2)..(2)
<223> OTHER INFORMATION: X= beta-alanine
<220> FEATURE:
<221> NAME/KEY: MISC_FEATURE
<222> LOCATION: (4)..(4)
<223> OTHER INFORMATION: C-terminal modification

<400> SEQUENCE: 11

Cys Xaa His Cys
1

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (2)..(2)
<223> OTHER INFORMATION: X= gamma-glutamyl
<220> FEATURE:
<221> NAME/KEY: MISC_FEATURE
```

```
<222> LOCATION: (4)..(4)
<223> OTHER INFORMATION: C-terminal amide group

<400> SEQUENCE: 12

Cys Xaa Cys Cys
1

<210> SEQ ID NO 13
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (2)..(2)
<223> OTHER INFORMATION: X= gamma-glutamyl
<220> FEATURE:
<221> NAME/KEY: MISC_FEATURE
<222> LOCATION: (3)..(3)
<223> OTHER INFORMATION: C-terminal amide group

<400> SEQUENCE: 13

Cys Xaa Cys
1

<210> SEQ ID NO 14
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (3)..(3)
<223> OTHER INFORMATION: C-terminal amide group

<400> SEQUENCE: 14

Cys Pro Cys
1

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (4)..(4)
<223> OTHER INFORMATION: C-terminal amide group

<400> SEQUENCE: 15

Cys Gly Pro Cys
1
```